(12) United States Patent
Murray et al.

(10) Patent No.: US 8,777,960 B2
(45) Date of Patent: Jul. 15, 2014

(54) INTERLOCK DRIVING INSTRUMENT

(75) Inventors: Nicole Murray, West Chester, PA (US); Frank Andrew Wilson, West Chester, PA (US); Kyle Henning, West Chester, PA (US); Sean Powell, West Chester, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 137 days.

(21) Appl. No.: 13/363,134

(22) Filed: Jan. 31, 2012

(65) Prior Publication Data
US 2012/0253355 A1    Oct. 4, 2012

Related U.S. Application Data

(63) Continuation-in-part of application No. 13/073,294, filed on Mar. 28, 2011, and a continuation-in-part of application No. PCT/US2011/030170, filed on Mar. 28, 2011.

(51) Int. Cl.
*A61B 17/58* (2006.01)
*A61B 17/60* (2006.01)
*A61F 2/00* (2006.01)

(52) U.S. Cl.
USPC .............................. 606/104; 606/99; 606/916

(58) Field of Classification Search
USPC .............. 606/99, 104, 915–916; 81/442–444, 81/448
See application file for complete search history.

(56) References Cited

U.S. PATENT DOCUMENTS

| 5,025,688 | A  | 6/1991 | Davis |
| 6,286,401 | B1 | 9/2001 | Hajianpour |
| 6,904,836 | B1 | 6/2005 | Andrei |
| 6,994,710 | B2 | 2/2006 | White et al. |
| 7,249,544 | B2 | 7/2007 | Totsu |
| 7,909,834 | B2 | 3/2011 | Selover |
| 2003/0236529 | A1 | 12/2003 | Shluzas et al. |
| 2005/0033307 | A1* | 2/2005 | Cook et al. ............ 606/104 |
| 2007/0010821 | A1 | 1/2007 | Wilkinson et al. |
| 2008/0215061 | A1 | 9/2008 | Schumacher et al. |
| 2009/0211412 | A1 | 8/2009 | Witte |

FOREIGN PATENT DOCUMENTS

| DE | 20014911 | 11/2000 |
| DE | 10042424 | 3/2002 |
| WO | WO 90/08510 | 8/1990 |
| WO | WO 2012/134437 | 10/2012 |
| WO | WO 2012/134628 | 10/2012 |

OTHER PUBLICATIONS

International Patent Application No. PCT/US2012/023376: International Search Report dated Apr. 11, 2012, 13 pages.

* cited by examiner

*Primary Examiner* — Andrew Yang
*Assistant Examiner* — Olivia C Chang
(74) *Attorney, Agent, or Firm* — Baker & Hostetler LLP

(57) ABSTRACT

An interlock driving instrument is configured to be releasably lockable to a fastener, such as a bone anchor. A bone anchor can be locked to the interlock driving instrument by inserting an expandable distal end of the shaft of the interlock driving instrument into the driving opening of the bone anchor and expanding the distal end within the driving opening by translating an expansion member into the expandable distal end. Alternatively, the bone anchor can be locked to the interlock driving instrument by inserting the distal end of the shaft of the interlock driving instrument into the driving opening of the bone anchor and translating a sliding member along a sloped surface defined in a channel extending into the shaft.

47 Claims, 23 Drawing Sheets

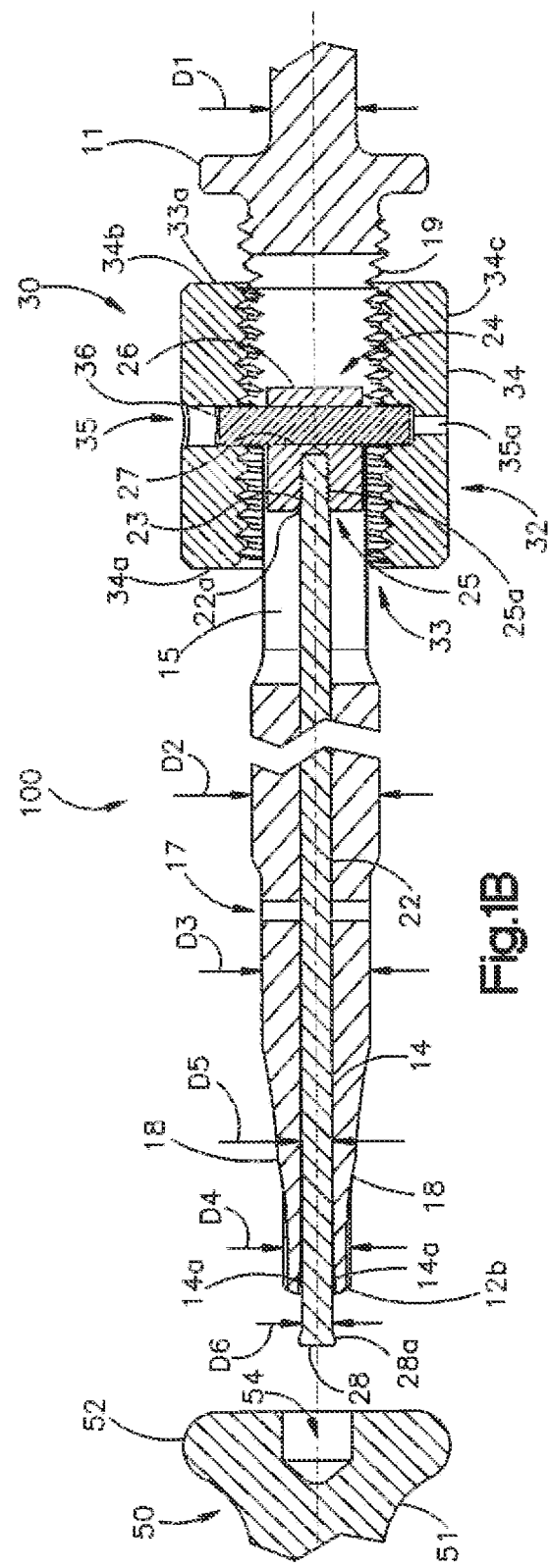

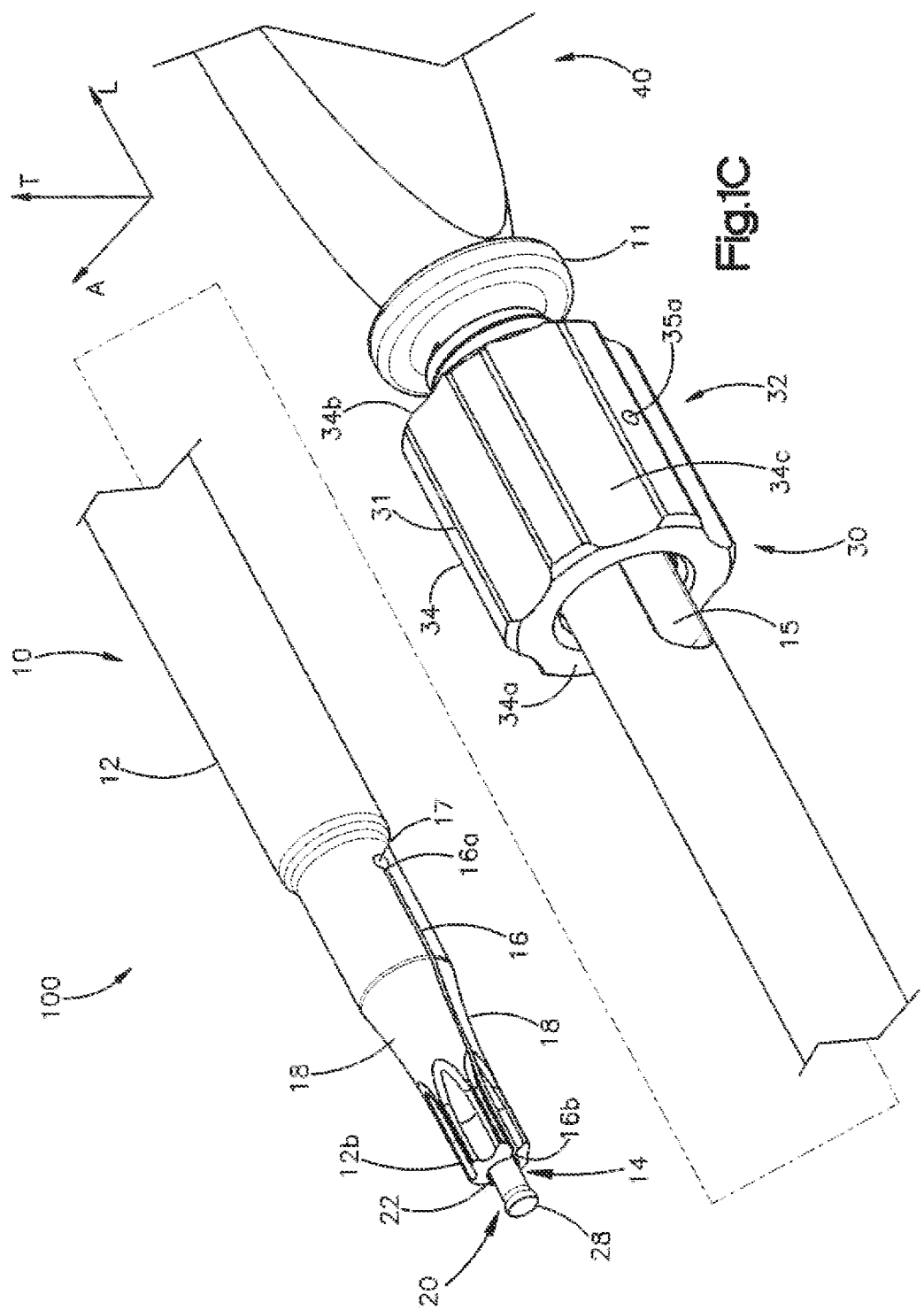

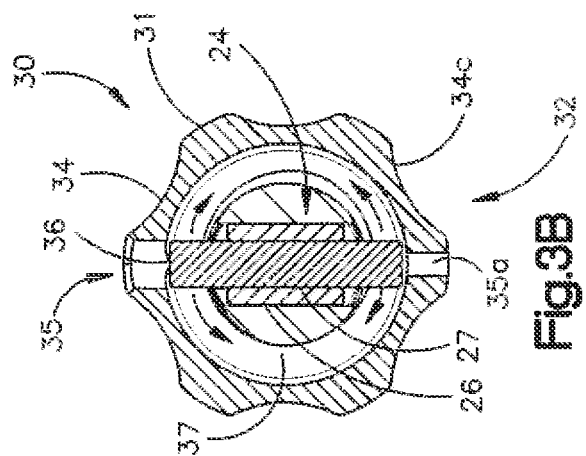
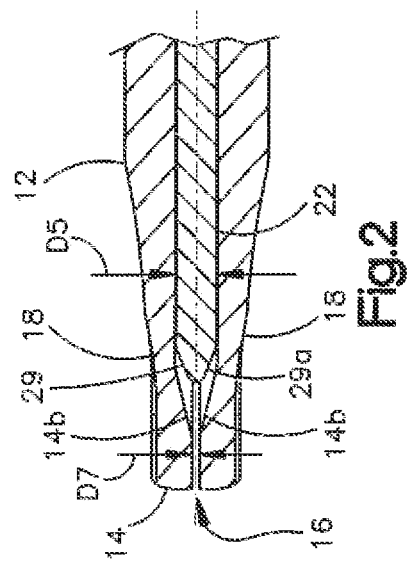
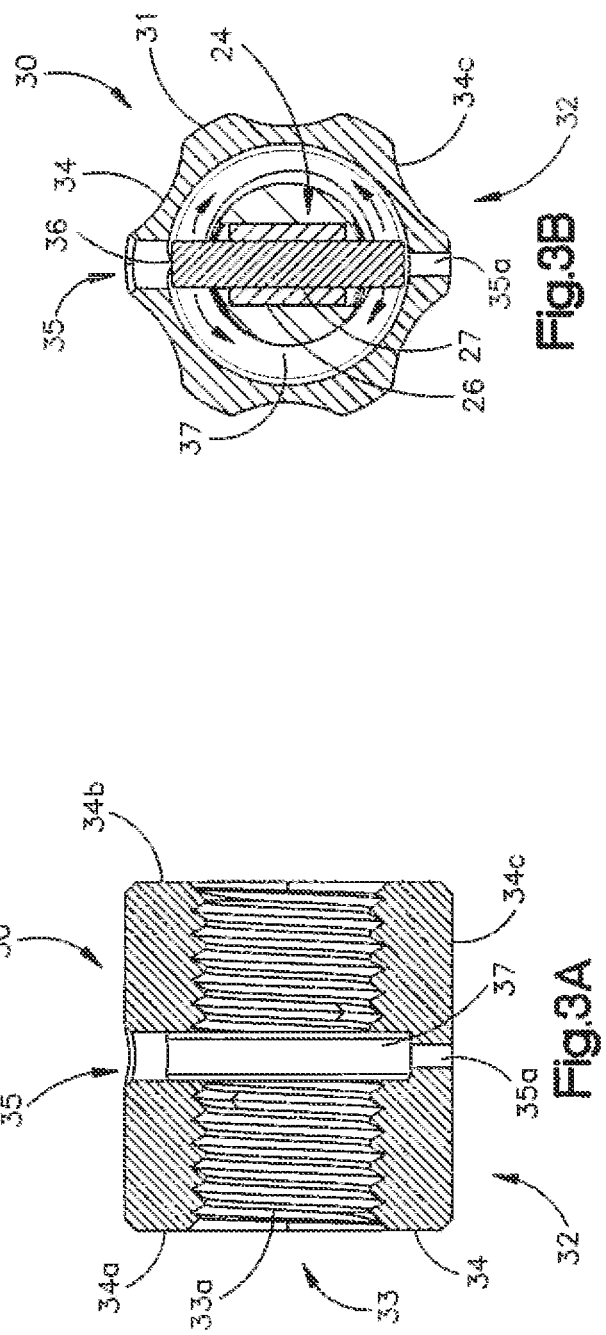

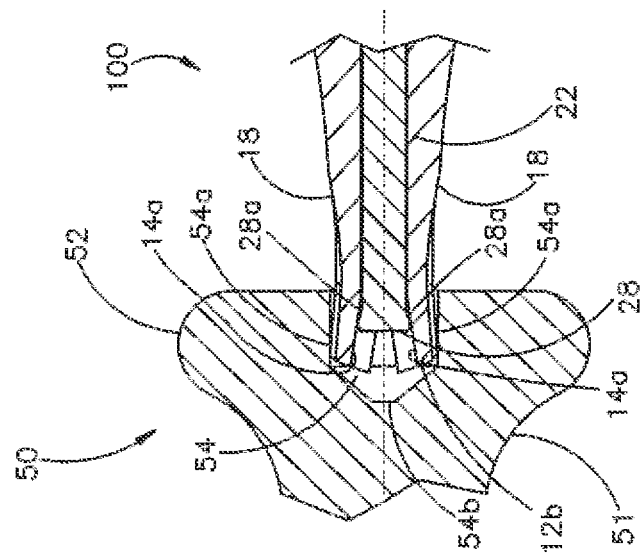
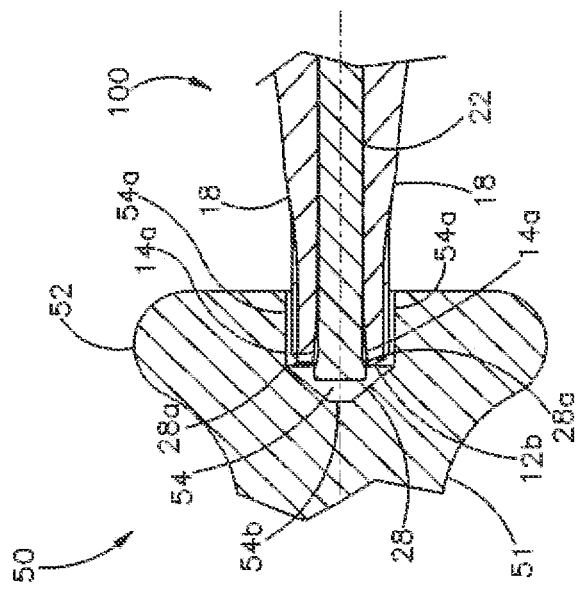

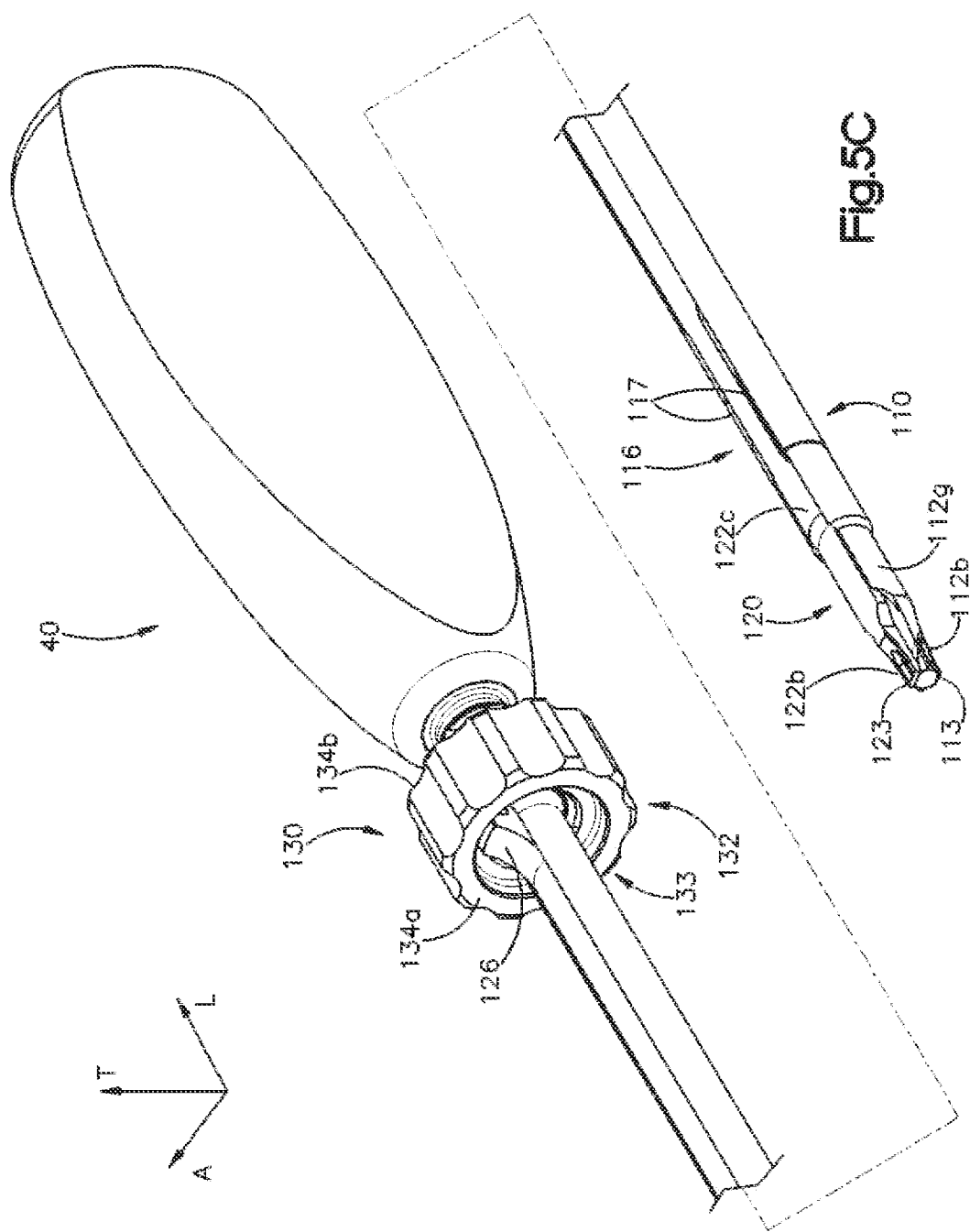

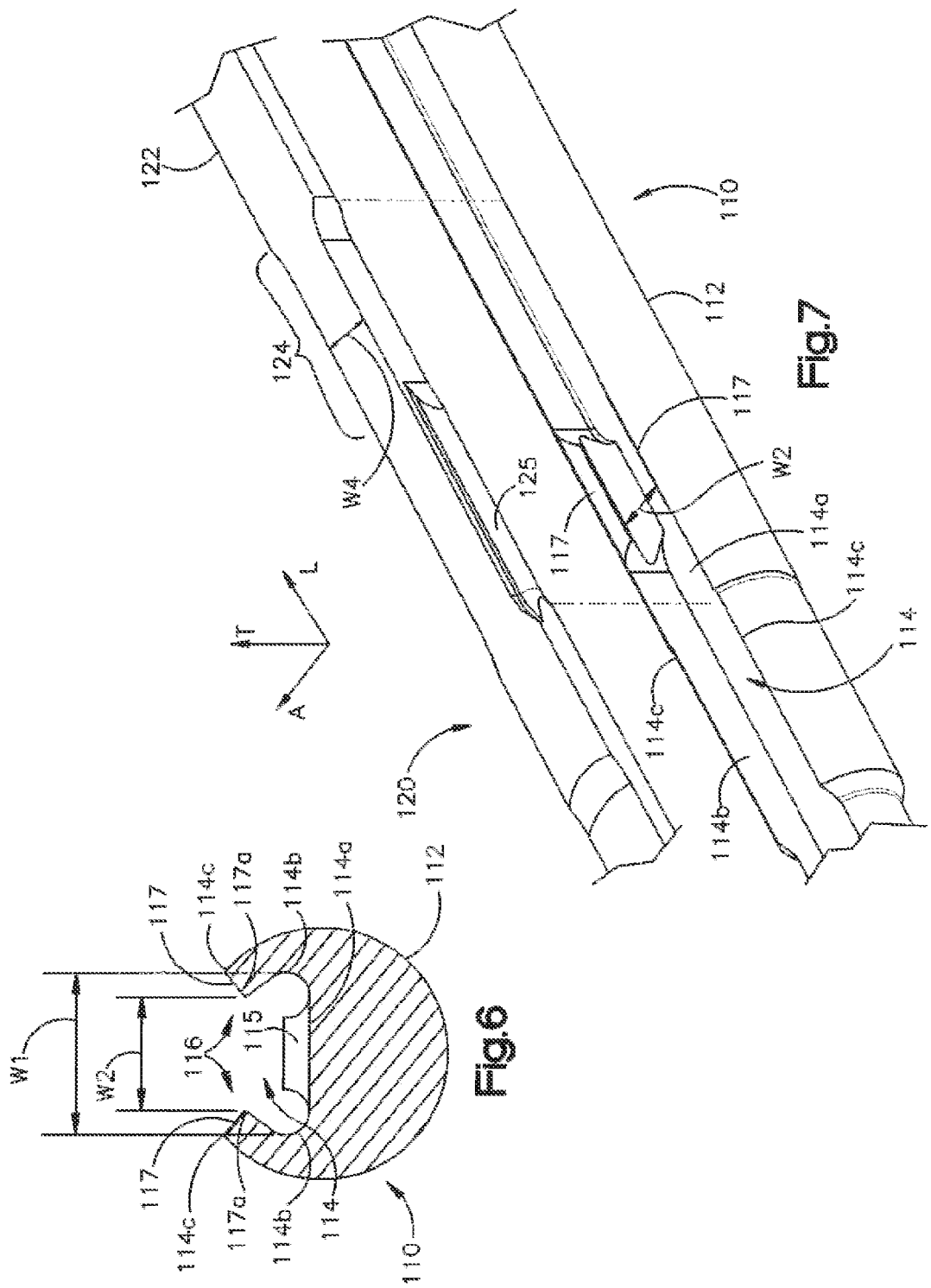

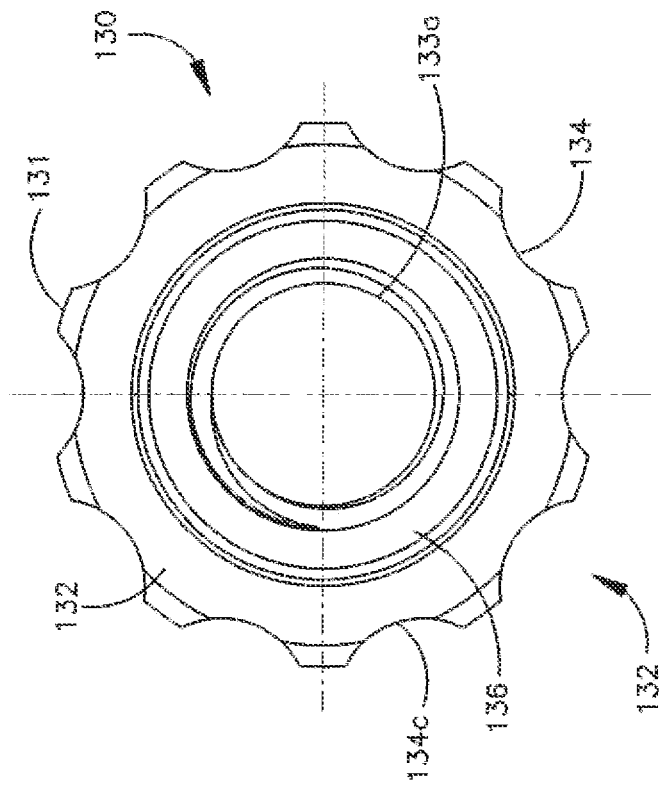
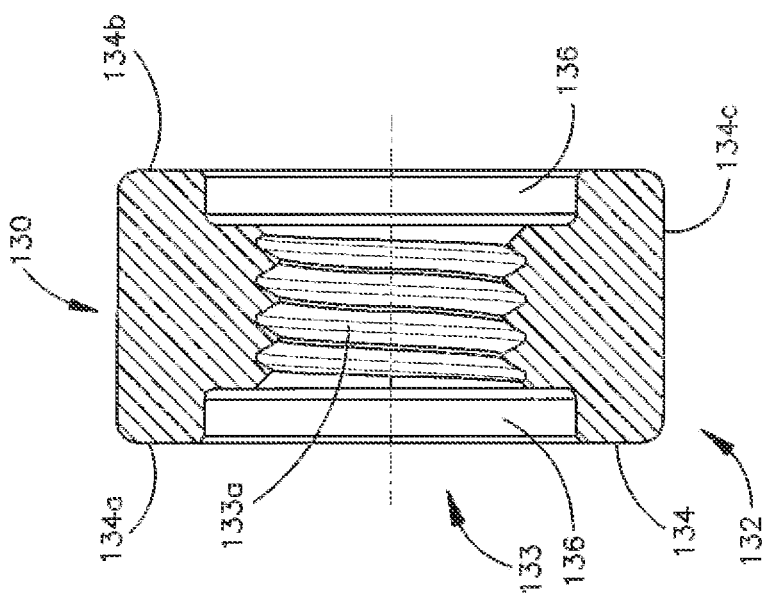

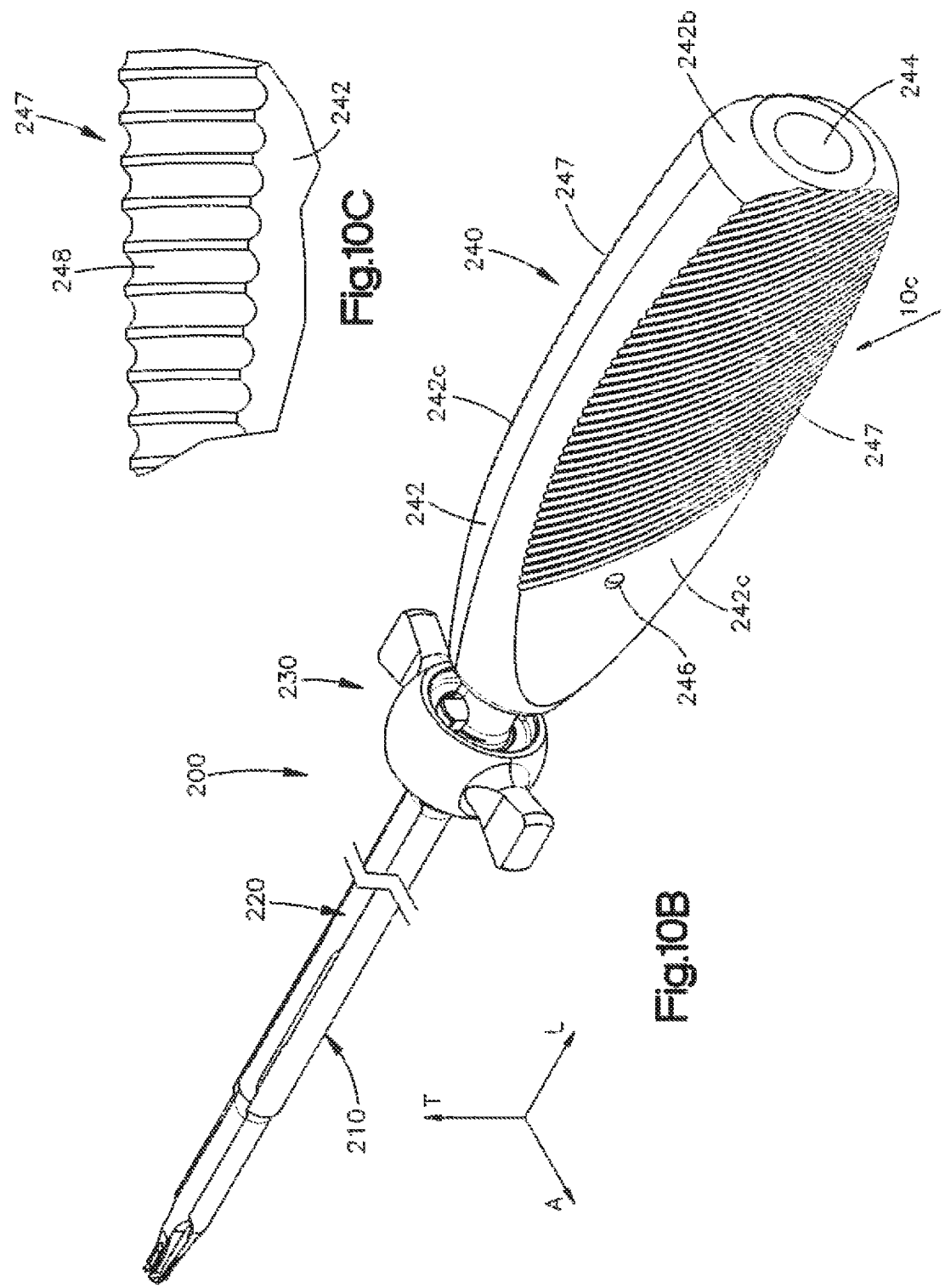

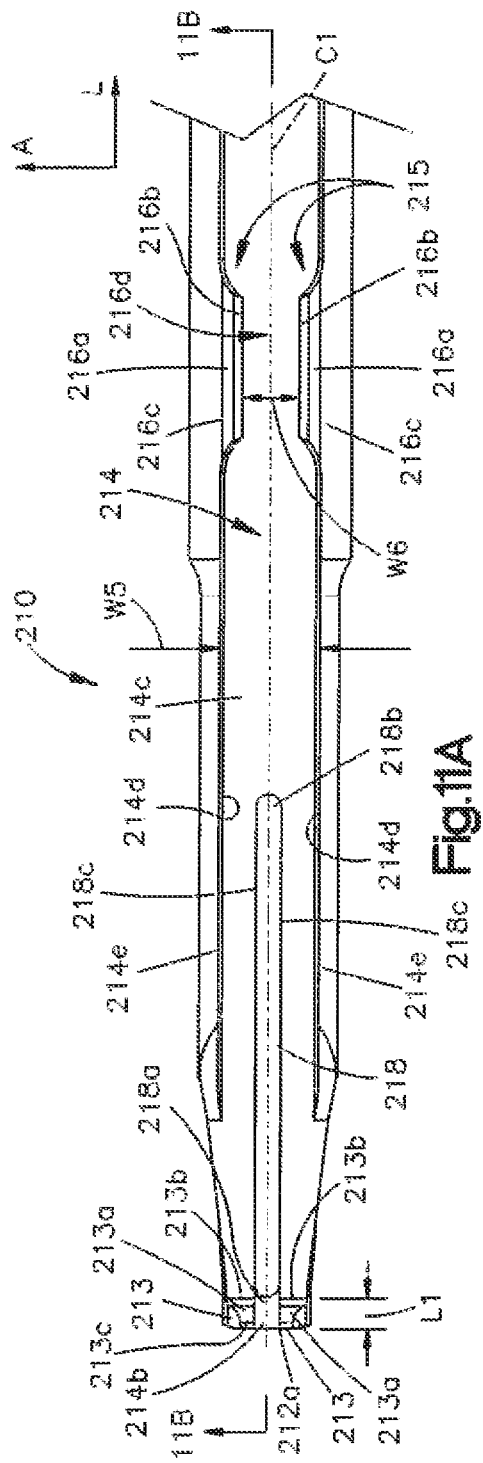
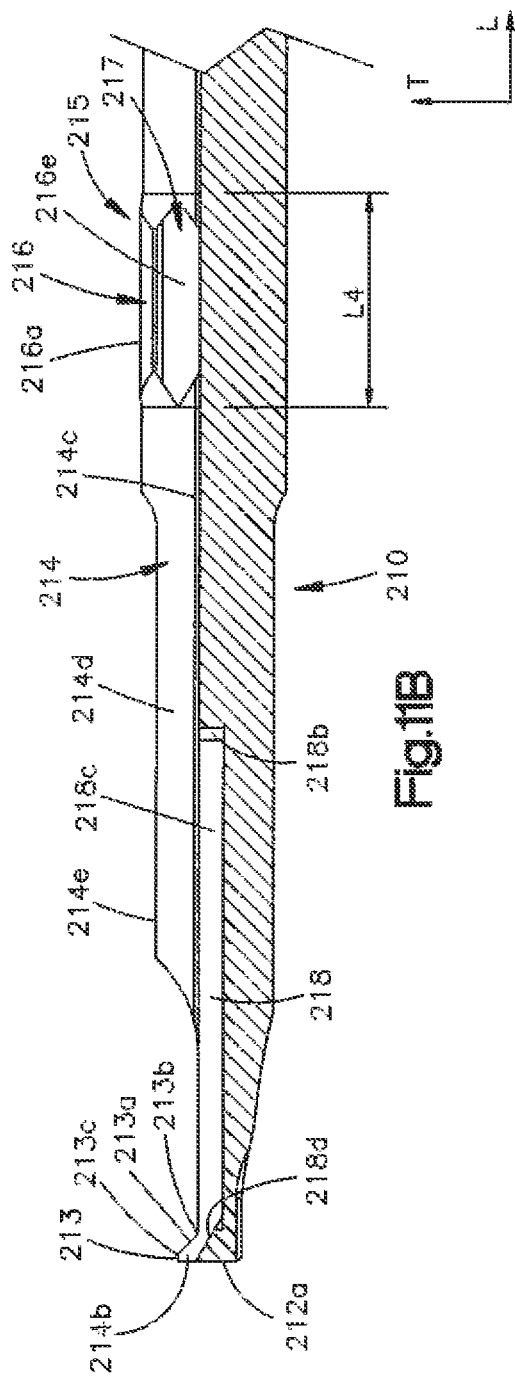
Fig.11A
Fig.11B

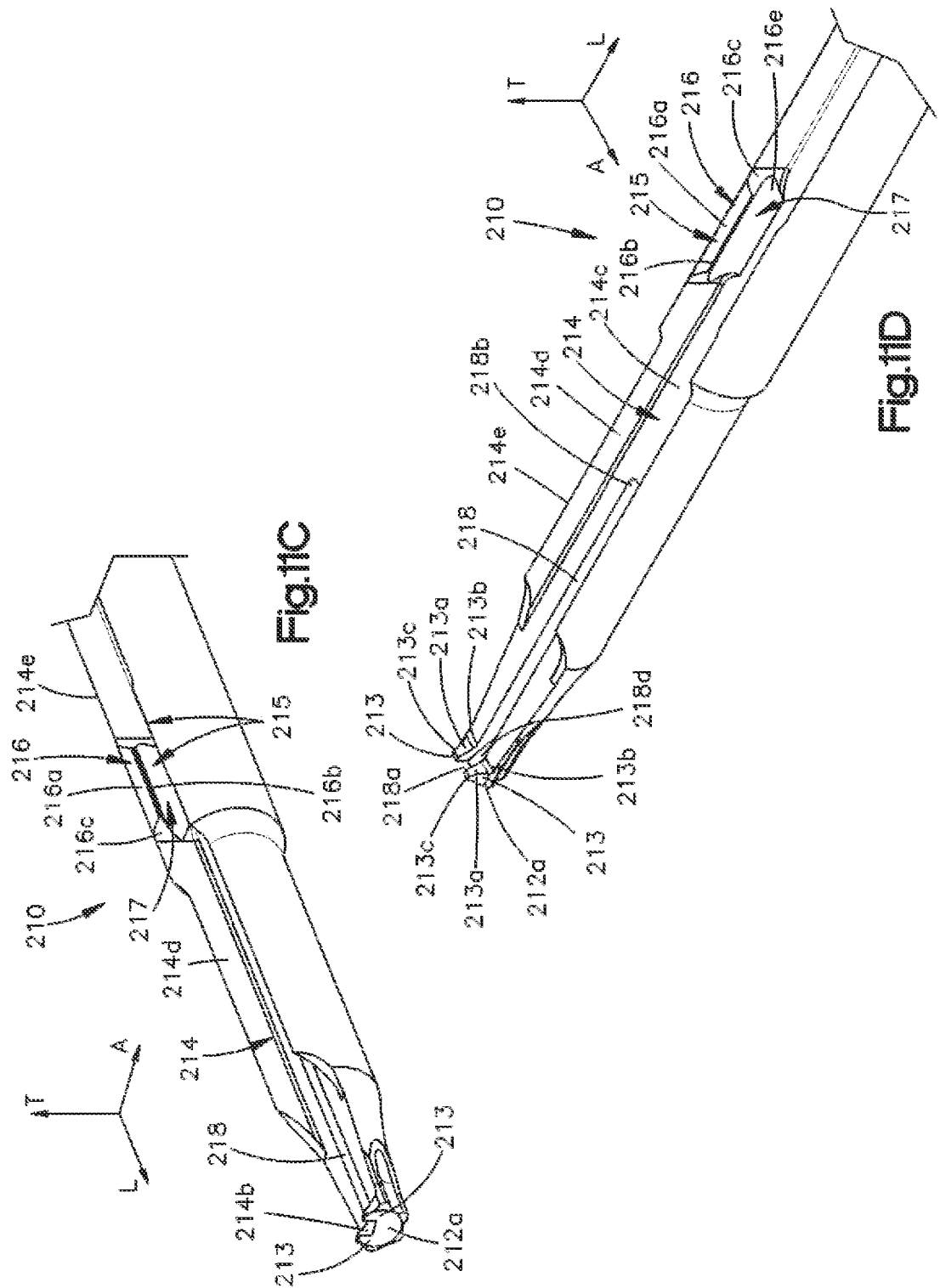

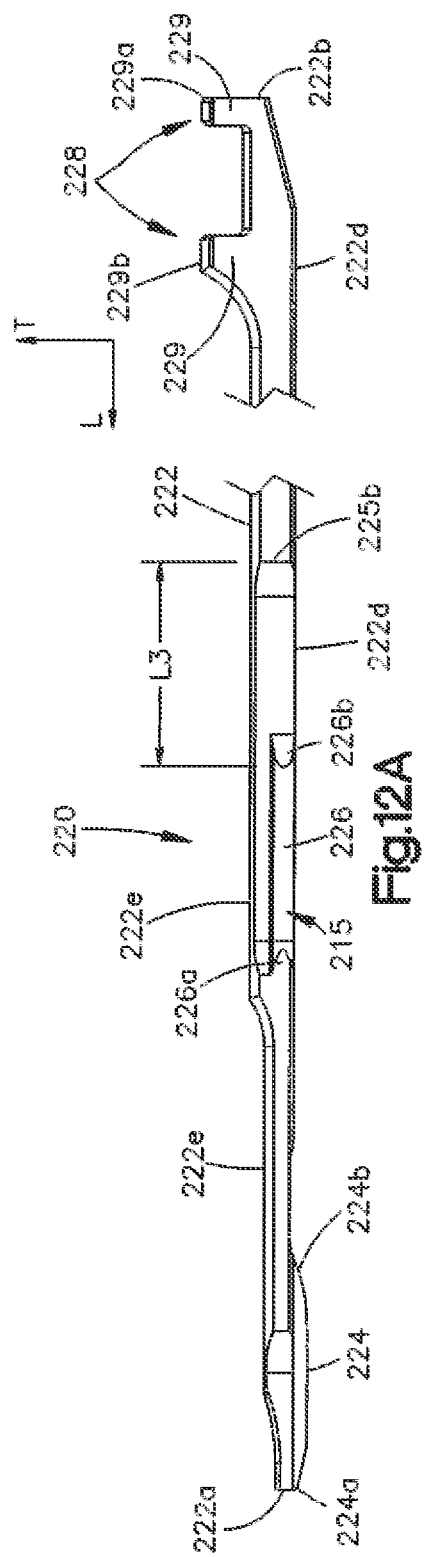
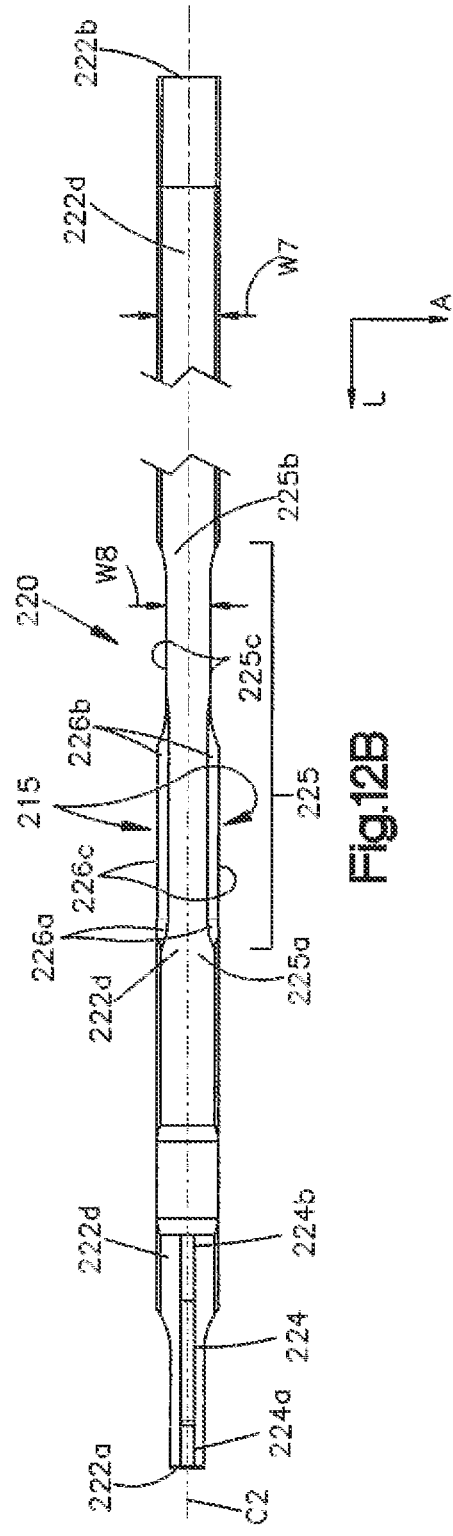
Fig.12A
Fig.12B

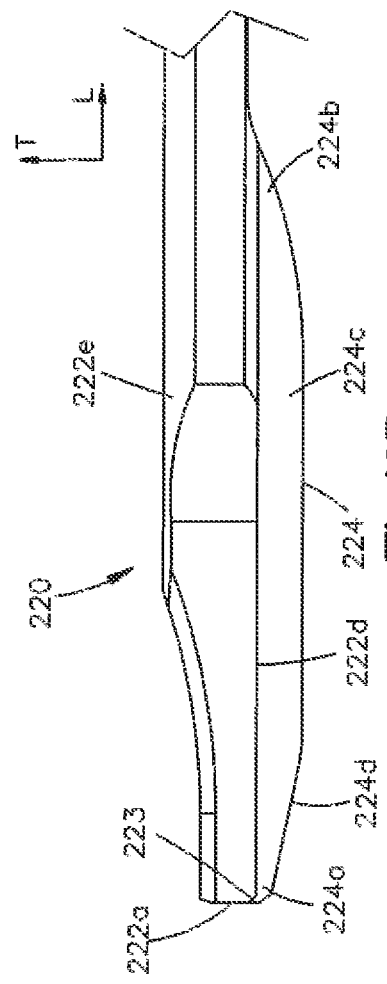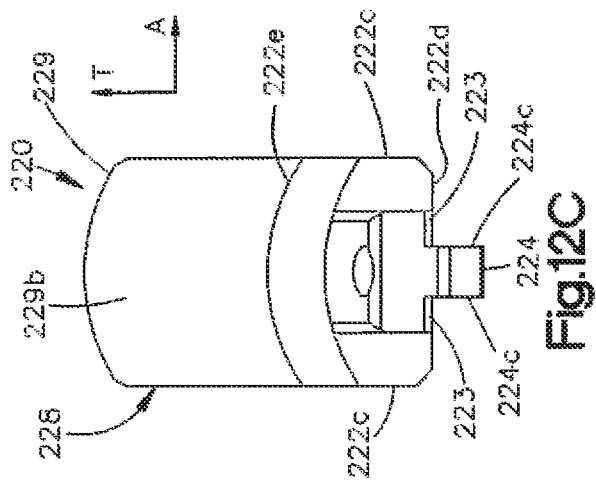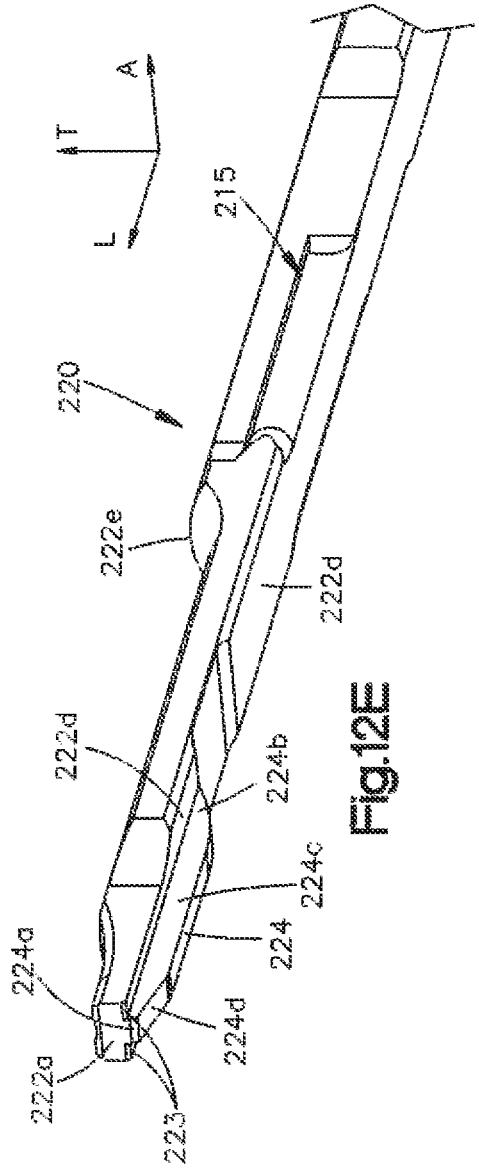

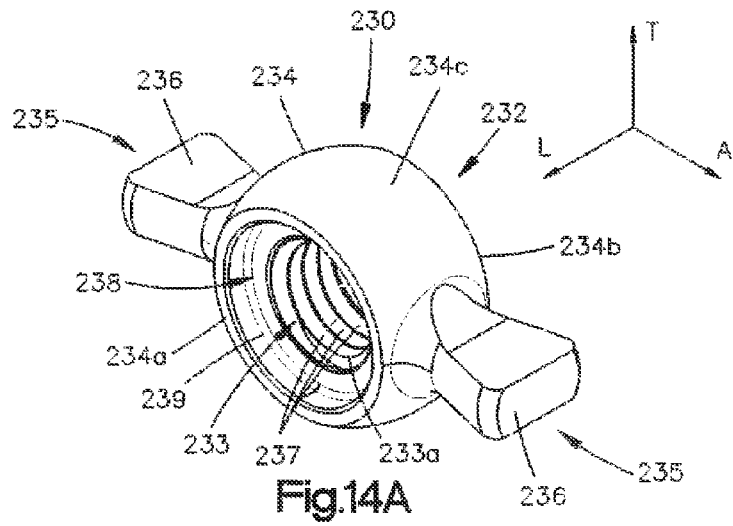
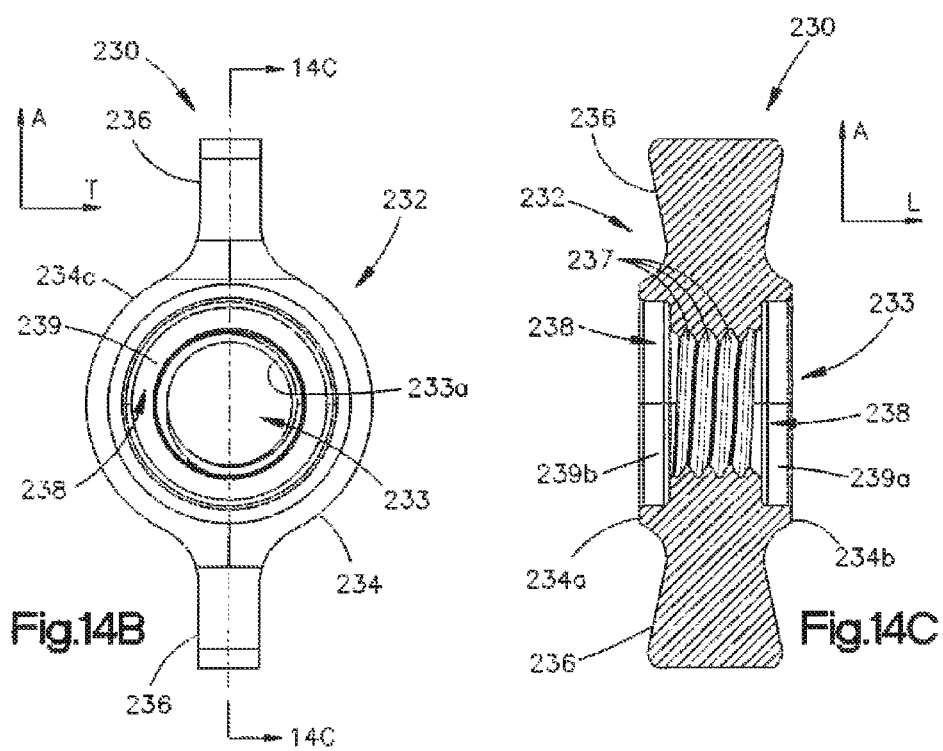

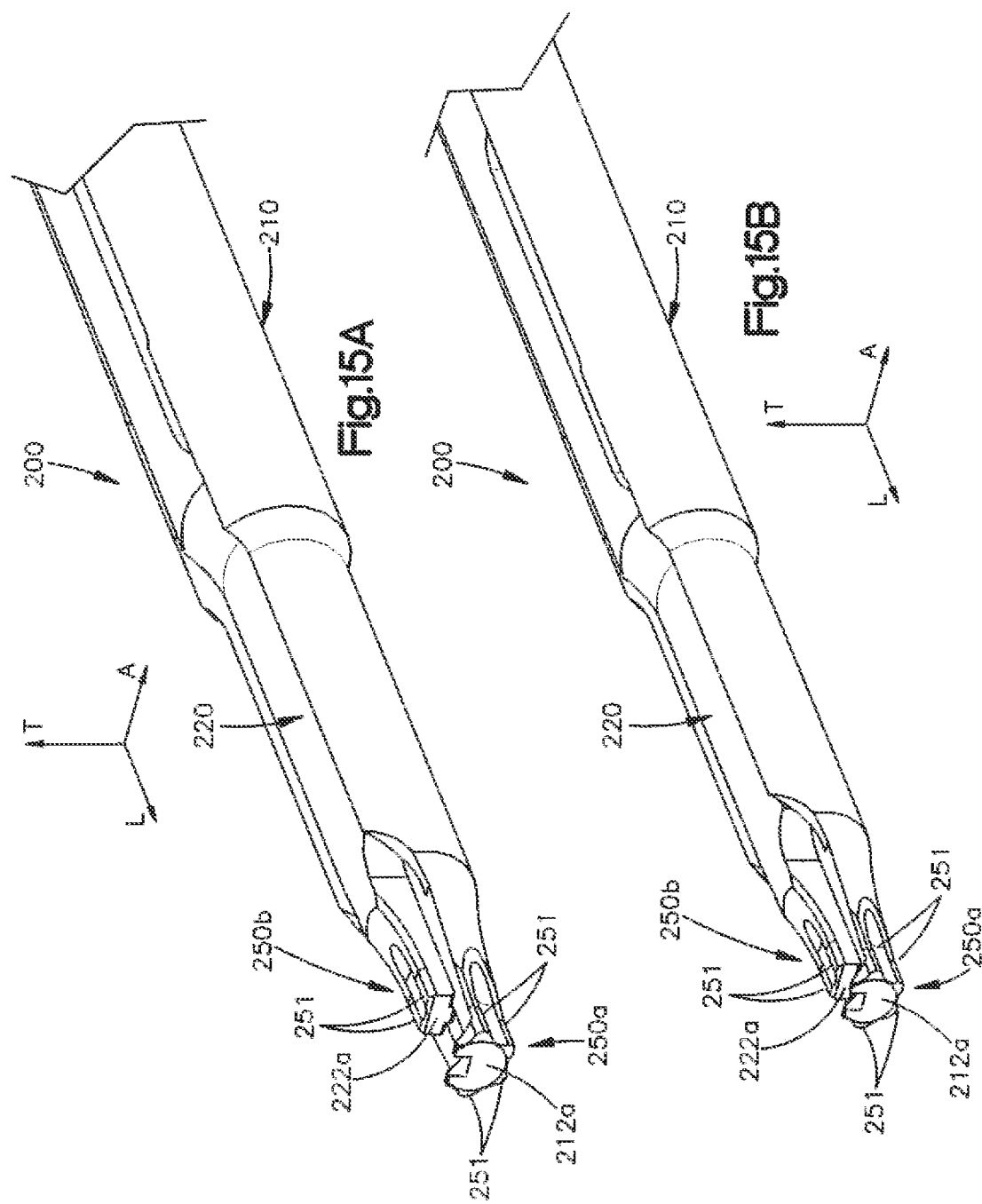

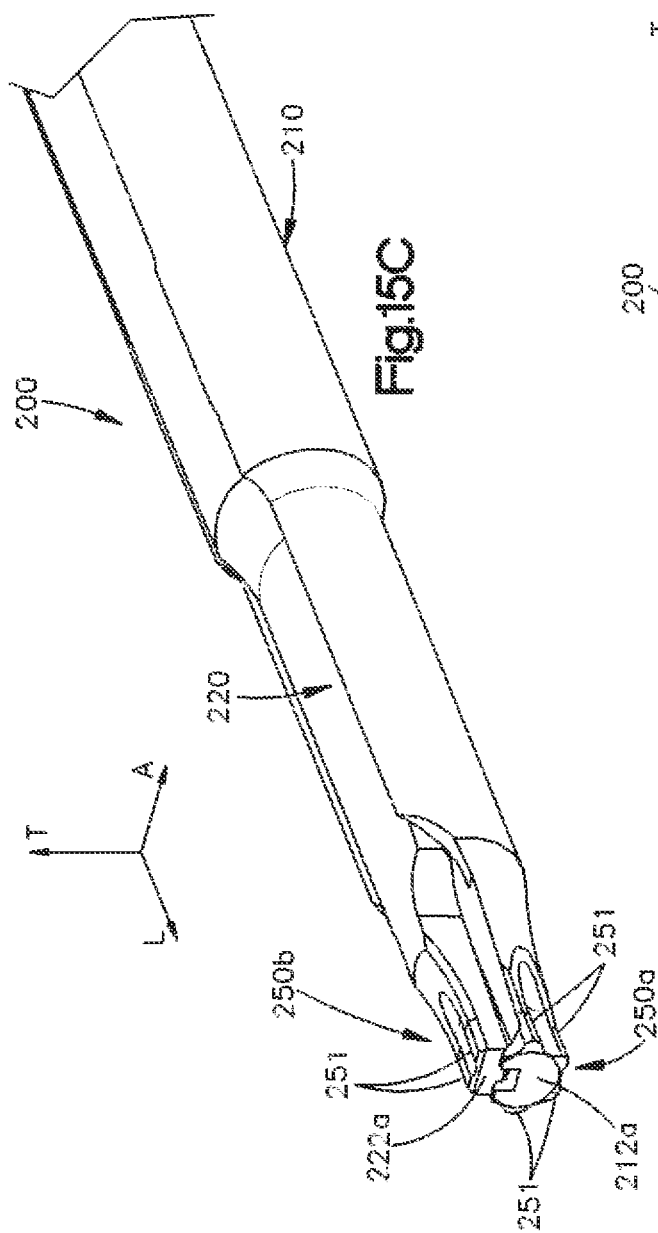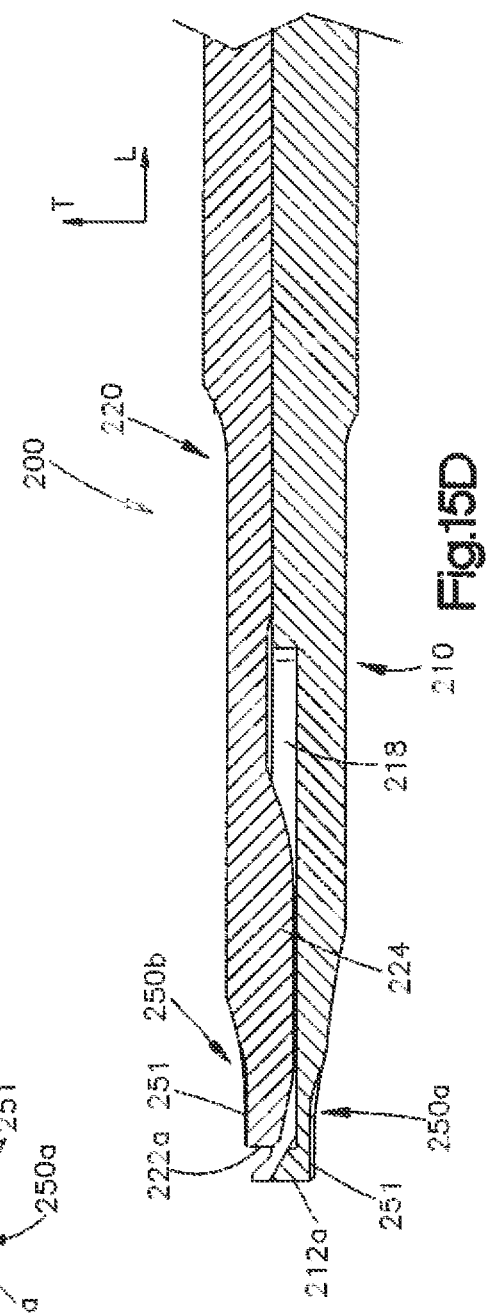

INTERLOCK DRIVING INSTRUMENT

CROSS-REFERENCE TO RELATED APPLICATIONS

This patent application is a continuation-in-part of and claims priority to U.S. patent application Ser. No. 13/073,294, filed Mar. 28, 2011 and is a continuation-in-part of and claims priority to international patent application number PCT/US2011/030170, filed Mar. 28, 2011, the disclosures of which are hereby incorporated by reference as if set forth in their entireties herein.

BACKGROUND

When small bone anchors, and in particular small bone screws, are inserted into or removed from a patient, there is typically a risk that the bone screws will become disengaged from the tip of the driving instrument and lost in the patient. Driving instruments to which small bone screws can be secured, or locked typically have retention sleeves or other structures mounted on the shafts of the driving instruments. These structures may cause the shaft of a driving instrument to have too large a diameter for a desired application, or may obscure a surgeon's view of the bone screw and/or the target insertion or removal location in the patient.

SUMMARY

In accordance with one embodiment, a locking screwdriver configured to drive a bone anchor into bone includes a shaft that defines a proximal end and a distal end that is spaced from the proximal end along a first direction. The distal end is configured to be received by a driving opening of the bone anchor. The shaft defines a first guide member that extends from the distal end toward the proximal end along the first direction. The shaft includes a plurality of ramps disposed at the distal end, each ramp defining a sloped surface that is angularly offset relative to the first direction. The locking screwdriver further includes a sliding member that includes a second guide member configured to engage the first guide member so as to direct the sliding member to translate along the shaft and onto each of the plurality of ramps to a releasably locked position. The locking screwdriver is releasably locked to the bone anchor when the sliding member and the distal end of the shaft are disposed in the driving opening and the sliding member is in the releasably locked position. The locking screwdriver further includes an actuator configured to apply a force that biases the sliding member to translate along the shaft to the releasably locked position.

BRIEF DESCRIPTION OF THE DRAWINGS

The foregoing summary, as well as the following detailed description of the preferred embodiments of the application, will be better understood when read in conjunction with the appended drawings. For the purposes of illustrating the interlock driving instrument, there are shown in the drawings preferred embodiments. It should be understood, however, that the instant application is not limited to the precise arrangements and/or instrumentalities illustrated in the drawings, in which:

FIG. 1B is a sectional elevation view of the interlock driving instrument illustrated in FIG. 1A in an assembled configuration;

FIG. 1C is a perspective view of the interlock driving instrument illustrated in FIG. 1A in an assembled configuration;

FIG. 2 is a sectional elevation view of selected components of the interlock driving instrument illustrated in FIG. 1A configured in accordance with an alternative embodiment;

FIG. 3A is a sectional elevation view of an actuator component of the interlock driving instrument illustrated in FIG. 1A;

FIG. 3B is a sectional elevation view of the actuator illustrated in FIG. 3A in an assembled configuration;

FIG. 4A is a sectional elevation view of the interlock driving instrument illustrated in FIG. 1A inserted into the head of a bone anchor, with the interlock driving instrument in an unlocked configuration;

FIG. 4B is a sectional elevation view of the interlock driving instrument inserted into the head of the bone anchor illustrated in FIG. 4A, with the interlock driving instrument in a releasably locked configuration;

FIG. 5C is a perspective view of the interlock driving instrument illustrated in FIG. 5A in an assembled configuration;

FIG. 6 is a sectional elevation view of a portion of the shaft of the interlock driving instrument illustrated in FIG. 5A;

FIG. 7 is a perspective view of respective portions of the shaft and the sliding member of the interlock driving instrument illustrated in FIG. 5A;

FIG. 8A is a sectional elevation view of an actuator component of the interlock driving instrument illustrated in FIG. 5A;

FIG. 8B is a front elevation view of the actuator of the interlock driving instrument illustrated in FIG. 5A;

FIG. 10B is an assembled perspective view of the interlock driving instrument illustrated in FIG. 10A;

FIG. 10C is a perspective view of a portion of a handle component of the interlock driving instrument illustrated in FIG. 10A;

FIG. 11A is a top elevation view of a portion of a shaft component of the interlock driving instrument illustrated in FIG. 10A;

FIG. 11B is a side section view of the portion of the shaft illustrated in FIG. 11A;

FIG. 11C is a perspective view of the portion of the shaft illustrated in FIG. 11A;

FIG. 11D is another perspective view of the portion of the shaft illustrated in FIG. 11A;

FIG. 12A is a side elevation view of a sliding member component of the interlock driving instrument illustrated in FIG. 10A;

FIG. 12B is a bottom elevation view of the sliding member illustrated in FIG. 12A;

FIG. 12C is a front elevation view of the sliding member illustrated in FIG. 12A;

FIG. 12D is a side elevation view of a portion of the sliding member illustrated in FIG. 12A;

FIG. 12E is a perspective view of a portion of the sliding member illustrated in FIG. 12A;

FIG. 14A is a perspective view of an actuator component of the interlock driving instrument illustrated in FIG. 10A;

FIG. 14B is a side elevation view of the actuator illustrated in FIG. 14A;

FIG. 14C is a front section view of the actuator illustrated in FIG. 14A;

FIG. 15A is a perspective view of a portion of the assembled interlock driving instrument illustrated in FIG. 10A, with the sliding member operated into a retracted position;

FIG. 15B is a side section view of the portion of the interlock driving instrument illustrated in FIG. 15A with the sliding member operated into a partially retracted position;

FIG. 15C is a perspective view of the interlock driving instrument illustrated in FIG. 10A, with the sliding member operated into the releasably locked position;

FIG. 15D is a side section view of the portion of the interlock driving instrument illustrated in FIGS. 15A-C;

DETAILED DESCRIPTION

Figure 1A:
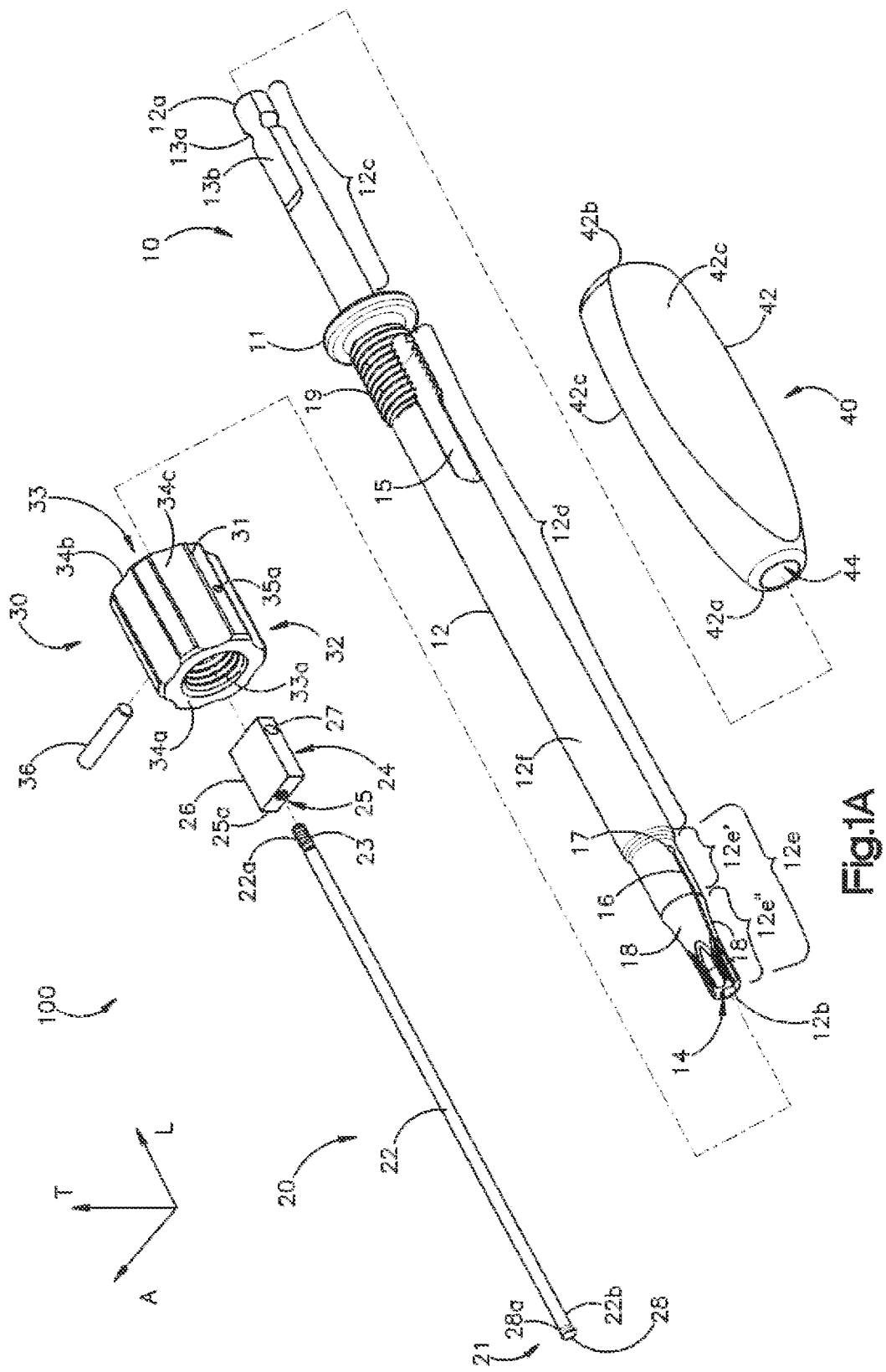
FIG. 1A is a perspective exploded view of an interlock driving instrument in accordance with an embodiment.

For convenience, the same or equivalent elements in the various embodiments illustrated in the drawings have been identified with the same reference numerals. Certain terminology is used in the following description for convenience only and is not limiting. The words "right", "left", "top" and "bottom" designate directions in the drawings to which reference is made. The words "inward", "inwardly", "outward", and "outwardly" refer to directions toward and away from the geometric center of the device and/or designated parts thereof. The terminology intended to be non-limiting includes the above-listed words, derivatives thereof and words of similar import.

Referring initially to FIGS. 1A-C, an interlock driving instrument 100, which can also be called a locking screwdriver or an interlock screwdriver, is configured to be releasably lockable to a fastener, such as a bone anchor and in particular a bone screw. For example, when small bone anchors such as small bone screws are inserted into or removed from a patient, a secure interface between the driving instrument and the head of the bone screw is desirable, for instance to prevent loss of the bone screw inside the patient were it to become disengaged from the driving instrument. A secure, or locked interface between a bone anchor 50 and the locking screwdriver 100 can be created by inserting an expandable distal end of the locking screwdriver 100 into the driving opening 54 in the head 52 of the bone anchor 50 and expanding the distal end within the driving opening. The locking screwdriver 100 generally comprises a number of components, for instance a shaft 10, an expansion member 20, an actuator 30, and a handle 40. The various components of the locking screwdriver 100 can be made of any suitable material, for instance commercially pure titanium, titanium alloy such as TAN, stainless steel, phenolic reinforced linen, silicon, Radel®, ultra-high-molecular-weight polyethylene (UHMW), and the like.

The shaft 10 is elongate in a longitudinal direction L, and defines a shaft body 12 that extends in the longitudinal direction L between a proximal end 12a and an opposing distal end 12b, the shaft body 12 having a generally cylindrical shape. The shaft body 12 can be constructed with one or more sections of varying cross-sectional dimension, or diameter. For instance, the shaft body 12 of the illustrated embodiment is constructed with a grip section 12c having a first diameter D1, an intermediate section 12d having a second diameter D2, and an expandable section 12e that includes a first subsection 12e' having a third diameter D3 and a second subsection 12e'' having a tapered diameter that decreases in length between the diameter D3 and a fourth diameter D4. In the illustrated embodiment, the length of the second diameter D2 is greater than the lengths of the first and third diameters D1 and D3, and the length of the fourth diameter D4 is shorter than the lengths of the first and third diameters D1-D3. It should be appreciated that the lengths of the diameters D1-D4 can be alternatively proportioned with respect to each other. It should further be appreciated that the shaft body 12 is not limited to a cylindrically shaped body, and that the shaft body 12 can be constructed with any suitable alternative shaft geometry. Moreover, it should further be appreciated that the shaft body 12 is not limited to the illustrated number of sections having varying diameters, and that the shaft body 12 can be alternatively constructed with any number of sections having uniform or varying diameters.

The grip section 12c of the shaft body 12 is configured to have a gripping structure, such as the handle 40, disposed thereon. The illustrated handle 40 includes a handle body 42 that extends longitudinally between opposing first and second ends 42a-b, respectively, and between opposing planar sides 42c, the handle body 42 having a generally cylindrical shape. It should be appreciated that the handle 40 can be constructed with any alternative handle body geometry. A longitudinal handle bore 44 extends into the handle body 42 from the first end 42a. The handle bore 44 is configured to receive the proximal end 12a of the shaft body 12 therein. The handle 40 can be affixed to the proximal end 12a of the shaft body 12 such that it will remain coupled to the shaft body 12 during operation of the locking screwdriver 100. For instance, the handle 40 can be affixed to the proximal end 12a of the shaft body 12 by inserting the proximal end 12a of the shaft body 12 into the handle bore 44 such that an engagement structure, such as an arced ridge defined on the inner surface of the handle bore 44, is disposed into the complimentary handle retaining groove 13a defined on the proximal end 12a of the shaft body 12.

The proximal end 12a of the shaft body 12 can define a keyed section 13b, the keyed section 13b configured to be received in a complimentary keyed section of the handle bore 44. Alignment of the keyed section 13b of the shaft body 12 within the complimentary keyed section of the handle bore 44 properly orients the handle 40 on the proximal end 12a of the shaft body 12. It should be appreciated that the handle 40, the handle retaining groove 13a, and the keyed section 13b of the illustrated embodiment are not meant to be limiting. For instance, the handle 40 can be supplemented and/or replaced by an alternative gripping structure of any appropriate size and/or shape. It should further be appreciated that the handle 40 and/or any other gripping structure can be alternatively affixed to the proximal end 12a of the shaft body 12 using any appropriate engagement and/or retention structures or methods. One or more separating structures, such as the disc 11, can extend radially outward from the shaft body 12 at one or more locations, for example at the location on the shaft 10 where the grip section 12c abuts the intermediate section 12d, as illustrated.

The expandable and intermediate sections 12e and 12d, respectively, of the shaft body 12 have a continuous bore extending therethrough in the longitudinal direction L, the bore defining a cannulation, or cannulated section 14, the cannulated section 14 configured to receive the expansion member 20 therein. The length of the cannulated section 14 in the longitudinal direction L is generally defined to be slightly longer than the corresponding length of the expansion member 20, such that the expansion member 20 can be fully disposed within the cannulated section 14. The cannulated section 14 has a uniform diameter D5 throughout, the diameter D5 having a slightly longer length than the diameter D6 of the expansion member 20, such that the expansion member 20 is translatable in the longitudinal direction L within the cannulated section 14 when disposed therein.

The expandable section 12e of the shaft body 12 is configured to be expanded by longitudinal translation of the expansion member 20 into the distal end 12b of the shaft body 12. When the distal end 12b of the shaft body 12 is disposed in the driving opening 54 of a bone anchor 50, such as a bone screw 51, the expandable section 12e can be expanded to create a locked interface between the locking screwdriver 100 and the bone screw 51, as described in more detail below. It should be appreciated that while the distal end 12b of the shaft body 12 is constructed with star drive driving structures configured for insertion into a bone screw with a complimentary star drive driving opening, the distal end 12b can be alternatively constructed for use with any other type of bone anchor driving opening.

A pair of diametrically opposing slots 16 are defined in the expandable section 12e of the shaft body 12, the slots 16 extending into the distal end 12b of the shaft body 12 between distal ends 16b and opposing proximal ends 16a, and extending through the shaft body 12 from the outer surface 12f into the cannulated section 14. The slots 16 divide the expandable section 12e of the shaft body 12 into opposing resilient expansion segments 18. The expansion segments 18 are outwardly deflectable with respect to each other in a transverse direction T that is substantially perpendicular to the longitudinal direction L, for instance when the expansion member 20 is longitudinally translated into the distal end 12b of the shaft body 12, as described in more detail below. A pair of expansion bores 17 can be defined in the shaft body 12, the expansion bores 17 extending through the shaft body 12 from the outer surface 12f of the shaft body 12 into the cannulated section 14. The expansion bores 17 of the illustrated embodiment are defined at the proximal ends 16a of the slots 16, and extend through the shaft body 12 in a lateral direction A that is substantially perpendicular to both the longitudinal direction L and the transverse direction T. The diameters of the bores 17 can be sized to enhance the flexibility of the expansion segments 18, for instance by lowering the amount of force required to deflect the expansion segments 18 outwardly away from each other. It should be appreciated that the slots 16 can be defined at any location around the circumference of the shaft body 12, such that they are or are not diametrically opposed with respect to each other. It should further be appreciated that one or more, such as a plurality of longitudinal slots 16 and/or corresponding expansion bores 17 can be defined in the expandable section 12e of the shaft body 12, thereby dividing the expandable section 12e of the shaft body 12 into a corresponding plurality of expansion segments 18.

The expansion member 20 of the illustrated embodiment comprises an expansion member such as an expansion rod 22 extending longitudinally between opposing first and second end 22a-b, respectively, the expansion rod 22 having a generally cylindrical shape. The expansion rod 22 is configured to be disposed within the cannulated section 14 of the shaft body 12. The expansion rod 22 has a uniform diameter D6 throughout, the diameter D6 having a slightly shorter length than the diameter D5 of the cannulated section 14, such that the expansion member 20 is translatable in the longitudinal direction L within the cannulated section 14 when disposed therein. The expansion rod 22 comprises an expansion tip 21 disposed at the second end 22b of the expansion rod 22, the expansion tip configured to deflect the expansion segments 18 outwardly away from each other when the expansion rod 22 is longitudinally translated into the distal end 12b of the shaft body 12. In the illustrated embodiment, the expansion tip 21 is constructed as a mandrel tip 28. The mandrel tip 28 defines a sloped surface 28a that is configured to deflect the expansion segments 18 radially outward away from each other as the expansion tip 21 is longitudinally translated into the distal end 12b of the shaft body 12, and thus into the cannulated section 14. The cannulated section 14 of the shaft body 12 can have a complimentary sloped surface 14a defined therein, for instance near the distal end 12b of the shaft body 12, the sloped surface 14a configured to engage with the sloped surface 28a of the mandrel tip 28 as the expansion tip 21 translates into the distal end 12b of the shaft body 12.

Referring now to FIG. 2, in an alternative embodiment the expansion tip 21 can be configured as a conical tip 29 having a conical surface 29a. The conical tip 29 is configured to deflect the expansion segments 18 radially outward away from each other as the expansion tip 21 is longitudinally translated into the distal end 12b of the shaft body 12 from within the cannulated section 14. As illustrated, the cannulated section 14 can be alternatively configured such that the cannulated section 14 has a narrowed section defining a sloped surface 14b near the distal end 12b of the shaft body 12. In particular, the diameter of the cannulated section 14 can be tapered in the narrowed section, for instance from the diameter D5 to a diameter D7 that has a shorter length than the diameter D5, such that the conical surface 29a of the conical tip 29 engages with the sloped surface 14b in the narrowed section of the cannulated section 14 as the expansion tip 21 translates into the distal end 12b of the shaft body 12, thereby causing the expansion segments 18 to radially deflect outwardly from each other. It should be appreciated that the expansion tip 21 can be integrally defined at the second end 22b of the expansion rod 22, or alternatively may be coupled to the second end 22b of the expansion rod 22, so as to be removable and/or replaceable.

Referring again to FIGS. 1A-C, the first end 22a of the expansion rod 22 is configured to be coupled to the actuator 30. In the illustrated embodiment, the expansion rod 22 is coupled to the actuator 30 via a coupling member in the form of the coupling block 26. Specifically, the coupling block 26 defines a body 24 and a longitudinal bore 25 that extends through the body 24 along the longitudinal direction L. The bore 25 is sized to receive the expansion rod 22, for instance at the first end 22a the expansion rod 22. Thus, the coupling block 26 is configured to receive the expansion rod 22. The inner surface of the bore 25 has a plurality of threads 25a defined therein, the threads 25a configured to engage with complimentary threads 23 defined along the outer surface of the first end 22a of the expansion rod 22, such that the expansion rod 22 can be attached to the coupling block 26 by screwing the first end 22a into the bore 25. The coupling block 26 further comprises a pin bore 27 extending therethrough along the lateral direction A, the pin bore 27 configured to receive a pin 36 that couples the coupling block 26 to the actuator 30. The shaft body 12 further comprises a block slot 15 defined therethrough, the block slot 15 extending through the shaft body 12 along the lateral direction A and sized to receive the coupling block 26 therein such that the coupling block 26 is translatable in the longitudinal direction L within the block slot 15. The block slot 15 is defined with a longitudinal length sufficient to allow the coupling block 26, and thus the expansion rod 22, to longitudinally translate within the block slot 15 as the locking screwdriver 100 is operated between unlocked and releasably locked configurations, as described in more detail below. It should be appreciated that while the illustrated coupling block 26 has a generally rectangular shape, the coupling block 26 can be alternatively configured with any appropriate shape. It should further be appreciated that the locking screwdriver 100 can be alternatively constructed with the coupling block 26 omitted, such that the expansion member 20, and in particular the expansion rod 22, can be directly coupled to the actuator 30.

Referring now to FIGS. 1A-C and 3A-B, the expansion member 20 is operatively coupled to the actuator 30, and the actuator 30 is operatively coupled to the shaft 10, such that when the actuator 30 is operated, the expansion member 20 is longitudinally translated within the cannulated section 14 of the shaft body 12. For example, in the illustrated embodiment, the actuator 30 is provided as a knob 32. The knob 32 comprises a knob body 34 that extends in the longitudinal direction L between opposing first and second ends 34a-b, respectively, the knob body 34 having a generally cylindrical shape. The knob body 34 defines a circumferential outer surface 34c. The outer surface 34c can have gripping structures, such as the ridges 31, defined thereon, the ridges 31 extending radially outward from the outer surface 34c.

The knob body 34 comprises a shaft bore 33 defined therethrough, the shaft bore 33 extending from the first end 34a through the second end 34b of the knob body 34 along the longitudinal direction L. The inner surface of the shaft bore 33 has a plurality of threads 33a defined therein, the threads 33a configured to rotatably engage with complimentary threads 19 defined on the outer surface 12f of the shaft body 12. The diameter of the shaft bore 33 has a length that is slightly longer than the length of the diameter D2 of the intermediate section 12d of the shaft body 12, such that the actuator 30 can be disposed on the shaft body 12 and the threads 33a of the actuator engaged with the threads 19 of the shaft body 12. It should be appreciated that the illustrated location of the threads 19 on the shaft body 12, and thus the location where the actuator 30 couples to the shaft 10, is not meant to be limiting, and that the interface between the shaft 10 and the actuator 30 can be located anywhere along the shaft 10 as appropriate. It should further be appreciated that the actuator 30 should not be limited to the knob 32, and that alternatively, any actuator that translates operation of the actuator into longitudinal translation of the expansion member 20 can be provided.

The knob body 34 further comprises a pin bore 35 defined therethrough, the pin bore 35 extending through diametrically opposed sides of the body 34 along the lateral direction A. The pin bore 35 is configured to receive the pin 36, the pin 36 configured to couple the expansion member 20, and in particular the coupling block 26, to the actuator 30. As depicted in FIGS. 3A-B, the knob body 34 further comprises an annular groove 37 that extends radially outward into the shaft bore 33, the annular groove 37 configured to allow rotation of the knob body 34 about the pin 36 during rotational operation of the knob 32. The pin bore 35 defines a narrowed section 35a on one of the opposing sides of the body 34, the narrowed section 35a extending from the bottom surface of the annular groove 37 through the outer surface 34c of the body, the narrowed section 35a configured with a diameter that is shorter in length than the diameter of the pin 36, such that when the pin 36 is inserted into the pin bore 35, the pin 36 abuts the narrowed section 35a such that the pin 36 is seated in the annular groove 37, and thus remains stationary with respect to the knob 32 during rotational operation of the knob 32. Specifically, when the coupling block 26 is disposed in the block slot 15 of the shaft body 12 and is operably coupled to the knob 32 by fully inserting the pin 36 into the pin bores 27 and 35, the pin 36 and the coupling block 26 can remain stationary with respect to the knob 32 while the knob 32 is rotated with respect to the shaft body 12.

Referring now to FIGS. 1A-C and 4A-B, in operation, a bone anchor 50, such as the bone screw 51, can be locked onto the locking screwdriver 100 for insertion and/or removal of the bone screw 51, for example into underlying bone of a patient. In particular, the distal end 12b of the shaft body 12 can be disposed into the driving opening 54 in the head 52 of the bone screw 51 and expanded, such that a secured, or locked, interface between the distal end 12b of the shaft body 12 and the driving opening 54 of the bone screw 51 is created. As necessary, the locking screw driver 100 can be operated to the non-expanded, or unlocked, configuration depicted in FIG. 4A. In the unlocked configuration, the mandrel tip 28, and in particular the sloped surface 28a, of the expansion rod 22 is located beyond the distal end 12b of the shaft body 12 such that the expansion segments 18 of the expandable section 12e of the shaft body 12 are in a relaxed, non-expanded position. The locking screwdriver 100 can be operated to the relaxed configuration by rotating the knob 32 of the actuator 30 in a direction about the shaft 10 that causes the threads 33a of the knob 32 to engage the complimentary threads 19 of the shaft 10 such that the actuator 30 longitudinally translates within the cannulated section 14 of the shaft 10 in a direction towards the distal end 12b of the shaft body 12. As the actuator 30 translates, the expansion member 20 (including the coupling block 26 and the expansion rod 22) is translated toward the distal end 12b of the shaft body 12 concurrently with the actuator 30. In this way, the mandrel tip 28 of the expansion rod 22 can be translated to a longitudinal location beyond the distal end 12b of the shaft body 12, as illustrated in FIG. 4A.

With the locking screwdriver 100 in the unlocked configuration, the distal end 12b of the shaft body 12 is inserted into the driving opening 54 in the head 52 of the bone screw 51. With the distal end 12b of the shaft body 12 inserted into the driving opening 54 of the bone screw 51, the locking screw driver 100 can be operated from the unlocked configuration to an expanded, or releasably locked configuration within the driving opening 54 of the bone screw 51. The locking screwdriver 100 can be operated to the releasably locked configuration by rotating the knob 32 of the actuator 30 about the shaft 10 in a direction that causes the threads 33a of the knob 32 to engage the complimentary threads 19 of the shaft 10 such that the actuator 30 longitudinally translates within the cannulated section 14 of the shaft 10 in a direction away from the distal end 12b of the shaft body 12 (i.e., the knob 32 is rotated in the direction opposite from the direction of rotation utilized to operate the locking screw driver 100 into the unlocked configuration). As the actuator 30 translates, the expansion member 20 (including the coupling block 26 and the expansion rod 22) is translated away from the distal end 12b of the shaft body 12 concurrently with the actuator 30. In this way, the mandrel tip 28 of the expansion rod 22 is translated into the distal end 12b of the shaft body 12, as illustrated in FIG. 4B.

As the mandrel tip 28 of the expansion rod 22 translates into the distal end 12b of the shaft body 12, the sloped surface 28a of the mandrel tip 28 rides along the complimentary sloped surfaces 14a of the cannulated section 14 of the shaft body 12, thereby causing the expansion segments 18 to radially deflect outwardly with respect to each other. As the mandrel tip 28 of the expansion rod 22 translates further into the distal end 12b of the shaft body 12, the outer surfaces 12f of the expansion segments 18 engage with the inner walls 54a of the driving opening 54 of the bone screw 51, imparting outwardly directed forces from the expansion segments 18 of the shaft body 12 to the driving inner walls 54a of the driving opening 54, and imparting inwardly directed forces from the inner walls 54a of the driving opening 54 to the expansion segments 18 of the shaft body 12 such that the driving opening 54 becomes locked in place on the expansion segments 18. The bone screw 51 can then be driven into or backed out of the underlying structure. When the bone screw 51 has been fully driven or removed, the actuator 30 can be operated to operate the locking screwdriver 100 to the unlocked configuration, wherein the distal end 12b of the shaft body 12 can be removed from the driving opening 54 of the bone screw 51. It should be appreciated that when operating the locking screwdriver 100 to the unlocked configuration, the actuator 30 can be advanced such that the expansion tip 21 of the expansion rod 22 abuts the bottom 54b of the driving opening 54 of the bone screw 51, thereby imparting a force from the expansion rod 22 to the head 52 of the bone screw 51, the force causing the bone screw 51 to be ejected from the distal end 12b of the shaft body 12.

Figure 5A:
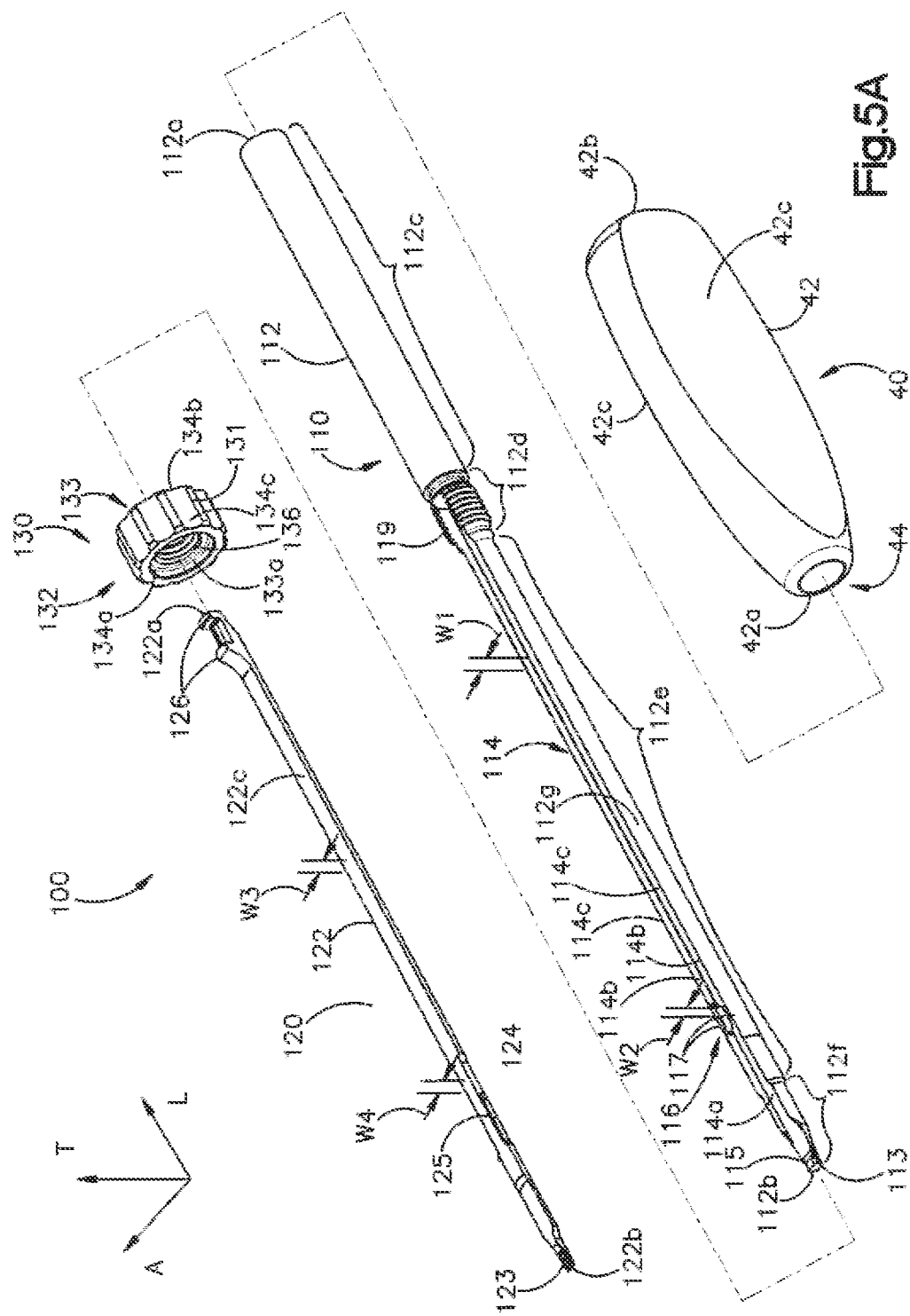
FIG. 5A is a perspective exploded view of the interlock driving instrument constructed in accordance with an alternative embodiment.
Figure 5B:
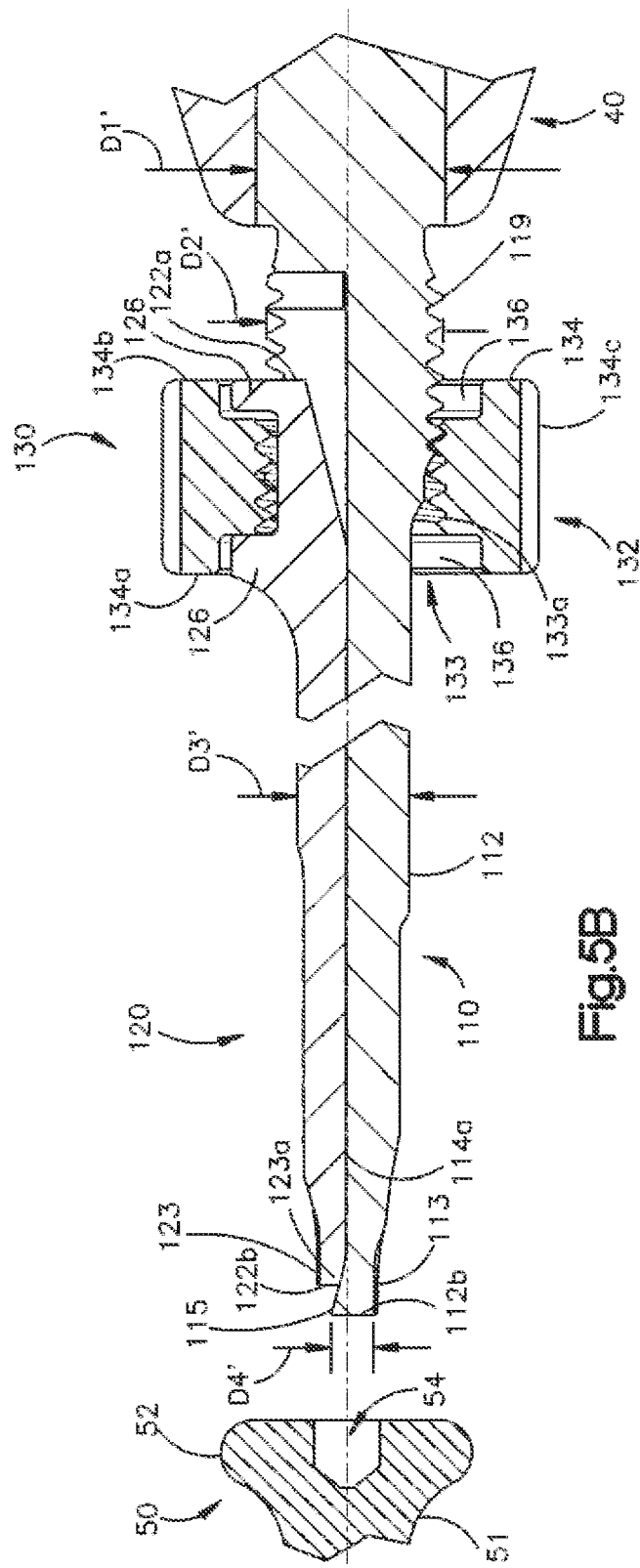
FIG. 5B is a sectional elevation view of the interlock driving instrument illustrated in FIG. 5A in an assembled configuration

Referring now to FIGS. 5A-C, the locking screwdriver 100 is illustrated in accordance with an alternative embodiment. A secured, or locked, interface between a bone anchor 50 and the illustrated embodiment of the locking screwdriver 100 can be created by inserting the distal end of the locking screwdriver 100 into the driving opening 54 of the bone anchor 50 and operating the locking screwdriver 100 to longitudinally advance a sliding member into the distal end of the locking screwdriver 100, as described in more detail below. The illustrated embodiment of the locking screwdriver 100 generally comprises a number of components, such as a shaft 110, a sliding member 120, an actuator 130, and a handle 40.

The shaft 110 is elongate in the longitudinal direction L, and defines a shaft body 112 that extends in the longitudinal direction L between a proximal end 112a and an opposing distal end 112b, the shaft body 112 having generally cylindrically shape. The shaft body 112 can be constructed with one or more sections of varying cross-sectional dimension, or diameter. For instance, the shaft body 112 of the illustrated embodiment is constructed with a grip section 112c having a first diameter D1', an actuator section 112d having a second diameter D2', an intermediate section 112e having a third diameter D3', and a tip section 112f having a tapered diameter that decreases in length between the diameter D3' and a fourth diameter D4'. In the illustrated embodiment, the length of the first diameter D1' is greater than the length of the second diameter D2', which is greater than the length of the third diameter D3', which is greater than the length of the fourth diameter D4'. It should be appreciated that the lengths of the diameters D1'-D4' can be alternatively proportioned with respect to each other. It should further be appreciated that the shaft body 112 is not limited to a cylindrically shaped body, and that the shaft body 112 can be constructed with any suitable alternative shaft geometry. Moreover, it should further be appreciated that the shaft body 112 is not limited to the illustrated number of sections having varying diameters, and that the shaft body 112 can be alternatively constructed with any number of sections having uniform or varying diameters.

The grip section 112c of the shaft body 112 is configured to have a gripping structure, such as the handle 40, disposed thereon. It should be appreciated that the handle 40 and/or any other gripping structure can be affixed to the proximal end 112a of the shaft body 112 using any appropriate engagement and/or retention structures or methods. The distal end 112b of the shaft body 112 can be constructed as a driving tip 113. The driving tip 113 and the driving tip 123 of the sliding member 120 can be respective driving structures defined thereon, the driving structures complimentary to the type of bone screw the locking screwdriver 100 is to be used with. For example, as depicted in FIG. 5C, the driving tips 113 and 123 have star drive structures defined thereon for insertion into a bone screw with a complimentary star drive driving opening. It should be appreciated that the driving tips 113 and/or 123 can be alternatively constructed with any other driving structures for use with respective alternative types of bone anchor driving openings.

The actuator, intermediate, and tip sections 112d, 112e, and 122f, respectively, of the shaft body 112 have a continuous longitudinal channel 114 defined therein, the channel 114 configured to receive the expansion member 120. The longitudinal length of the channel 114 is generally defined to be slightly longer than the longitudinal length of the sliding member 120, such that the sliding member 120 can be fully disposed within the channel 114. The channel 114 is configured as an open channel of rectangular cross section that has a bottom surface 114a and opposing side surfaces 114b that extend perpendicularly in the transverse direction T between the bottom surface 114a and respective upper edges 114c that are defined along the intersection of the side surfaces 114b with the outer surface 112g of the shaft body 112. The channel has a width W1 in the lateral direction A that is shorter than the length of the diameter D3'. The cross-sectional geometry of the channel 114 is configured such that the sliding member 120 is translatable in the longitudinal direction L within the channel 114 when disposed therein. It should be appreciated that the channel 114 is defined with a generally rectangular cross section so as to conform with the generally rectangular cross section of the sliding member 120, and that other appropriate channel geometries can alternatively be defined, for example to conform with sliding members 120 that are constructed in accordance with an alternative embodiment. The bottom surface 114a of the channel 114 has a sloped surface 115 defined between the distal end 112b of the shaft body 112 and a transition of the sloped surface 115 into the bottom surface 114a, the sloped surface 115 configured such that the sliding member 120 rides along the sloped surface 115 when the sliding member 120 is longitudinally translated into the distal end 112b of the shaft body 112. It should be appreciated that the sloped surface 115 is not limited to the straight surface of the illustrated embodiment. For instance, the sloped surface 115 can be curved between the distal end 112b and the transition into the bottom surface 114a, or can be alternatively defined using any other surface geometry.

The shaft body 112 further comprises retaining members 116, the retaining members 116 configured to retain the sliding member 120 within the channel 114. As depicted in FIG. 6, the retaining members 116 of the illustrated embodiment are defined as a pair of opposing arc shaped, or arced, protrusions 117 that extend inwardly from the side surfaces 114b on opposing sides of the channel 114. The protrusions 117 extend inwardly to ends 117a. The ends 117a of the protrusions 117 are separated by a gap that has a width W2 that is shorter in length than the width W1 of the channel 114. It should be appreciated that the retaining members 116 are not limited to the protrusions 117, and that one or more retaining members 116 can be alternatively defined utilizing any appropriate structure and/or geometry.

Referring again to FIGS. 5A-C, the sliding member 120 of the illustrated embodiment includes a sliding member body, or body 122 that extends longitudinally between a proximal or first end 122a and an opposed second or distal end 122b that is spaced from the first end 122a along longitudinal direction L. The body 122 can define any cross-section as desired, and defines a substantially rectangular cross section in accordance with the illustrated embodiment. The body 122 defines a width W3 in the lateral direction A that is slightly shorter in length than the width W1 of the channel 114 of the shaft body 112, such that when the sliding member 120 is disposed in the channel 114, the sliding member 120 is slidable, or translatable, in the longitudinal direction L within the channel 114. The cross-sectional geometry of the upper surface 122c of the body 122 can be defined to match the cross-sectional geometry of the outer surface 112g of the shaft body 112 when the sliding member 120 is disposed in the channel 114. For instance, in the illustrated embodiment, the upper surface 122c of the body 122 is curved to match the curvature of the upper surface 122c of the body 122.

The first end 122a of the sliding member 120 is configured to be coupled to the actuator 130. Specifically, the body 122 comprises one or more coupling members, such as the tabs 126 defined on the first end 122a of the body 122. The tabs 126 extend upwardly in the transverse direction T from the upper surface 122c of the body 122, the tabs 126 configured to be received in respective complimentary annular grooves 136 defined in the actuator 130, as described in more detail below. The body 122 further comprises a driving tip 123 defined at the second end 122b of the body 122. As described above, the driving tip 123 can be constructed with driving structures defined thereon, such as the illustrated star drive driving structures, that are complimentary to the type of bone screw the locking screwdriver 100 is to be used with. The driving tip 123 is configured to ride along the sloped surface 115 of the channel 114 such that the driving tip 123 is deflected radially upward within the channel 114 when the second end 122b of the sliding member 120 is longitudinally translated into the distal end 112b of the shaft body 112, as described in more detail below. The driving tip 123 can have a complimentary sloped surface 123a defined in its bottom surface, the sloped surface 123a configured to engage with the sloped surface 115 of the channel 114. It should be appreciated that the sloped surface 123a is not limited to a straight surface. For instance the sloped surface 123a can be curved, or can be defined using any other surface geometry.

Referring now to FIG. 7, the body 122 further comprises a narrowed section 124, the narrowed section 124 having a width W4 in the lateral direction A that is slightly shorter than the width W2 of the gap between the protrusions 117, such that when the sliding member 120 is disposed into the channel 114, the narrowed section 124 of the body 122 can fit through the gap between the protrusions 117. The body 122 further comprises a pair of longitudinal wings 125 defined in the body 122, the wings 125 extending in the longitudinal direction L between the narrowed section 124 and the second end 122b of the body 122. The wings 125 are configured to be nested in sliding engagement within the protrusions 117. During operation of the locking screwdriver 100 between unlocked and releasably locked configurations, described in more detail below, the outer surfaces of the wings 125 engage with the inner surfaces of the protrusions 117, thereby retaining the sliding member 120 within the channel 114. The wings 125 are defined with longitudinal lengths sufficient to maintain the nested engagement of the wings 125 within the protrusions 117 as the locking screwdriver 100 is operated between unlocked and releasably locked configurations.

Referring now to FIGS. 5A-C and 8A-B, the sliding member 120 is operatively coupled to the actuator 130, and the actuator 130 is operatively coupled to the shaft 110, such that when the actuator 130 is operated, the sliding member 120 is longitudinally translated within the channel 114 of the shaft body 112. For example, in the illustrated embodiment the actuator 130 is provided as a knob 132. The knob 132 comprises a knob body 134 that extends in the longitudinal direction L between opposing first and second ends 134a-b, respectively, the knob body 134 having a generally cylindrical shape. The knob body 134 defines a circumferential outer surface 134c. The outer surface 134c can have gripping structures, such as the ridges 131, defined thereon, the ridges 131 extending radially outward from the outer surface 134c.

The knob body 134 comprises a shaft bore 133 defined therethrough, the shaft bore 133 extending from the first end 134a through the second end 134b of the body along the longitudinal direction L. The inner surface of the bore 133 has a plurality of threads 133a defined therein, the threads 133a configured to rotatably engage with a complimentary threads 119 defined on the outer surface 112g of the shaft body 112. The diameter of the bore 133 has a length that is slightly longer than the length of the diameter D2' of the actuator section 112d of the shaft body 112, such that the actuator 130 can be disposed on the shaft body 112 and the threads 133a of the actuator engaged with the threads 119 of the shaft body 112. It should be appreciated that the illustrated location of the threads 119 on the shaft body 112, and thus the location where the actuator 130 couples to the shaft 110, is not meant to be limiting, and that the interface between the shaft 110 and the actuator 130 can be located anywhere along the length of the shaft 110 as appropriate. It should further be appreciated that the actuator 130 should not be limited to the knob 132, and that alternatively, any actuator that translates operation of the actuator into longitudinal translation of the sliding member 120 can be provided.

The knob body 134 further comprises a coupling interface, the coupling interface configured to couple the sliding member 120 to the actuator 130 when complimentary coupling members, such as the tabs 126, are received in the coupling interface. In the illustrated embodiment, the coupling interface comprises a pair of annular grooves 136 that extend inwardly into the knob body 134 from the first and second ends 134a-b, respectively. The annular grooves 136 are configured to allow rotation of the knob body 134 about the tabs 126 during rotational operation of the knob 132. Specifically, when the tabs 126 are disposed in the respective annular grooves 136, the sliding member 120 can remain stationary with respect to the knob 132 while the knob 132 is rotated with respect to the shaft body 112.

Referring now to FIGS. 5A-C and 9A-B, in operation, a bone anchor 50, such as the bone screw 51, can be locked onto the locking screwdriver 100 for insertion and/or removal of the bone screw 51, for example into underlying bone of a patient. The bone screw 51 can be locked onto the locking screwdriver 100 by inserting the driving tips 113 and 123 into the driving opening 54 of the bone screw 51 and operating the locking screwdriver 100 into the releasably locked configuration.

Figure 9A:
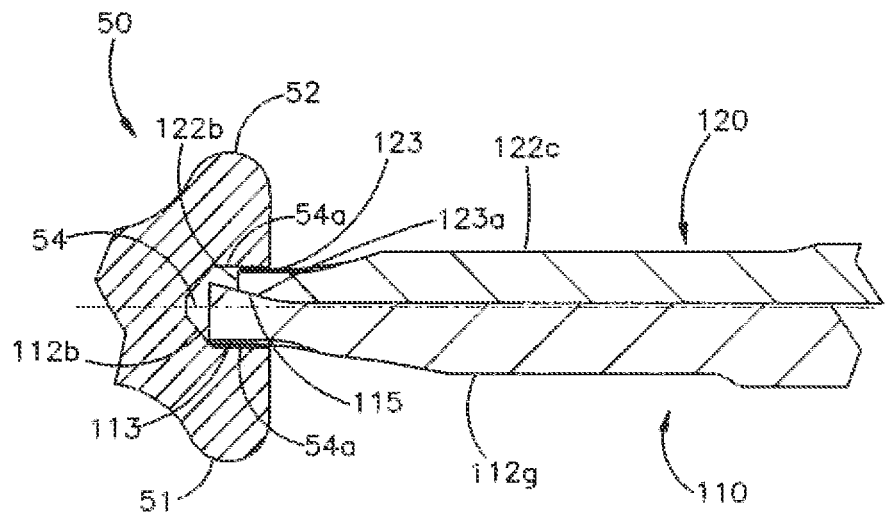
FIG. 9A is a sectional elevation view of the interlock driving instrument illustrated in FIG. 5A inserted into the head of a bone anchor, with the interlock driving instrument in an unlocked configuration.
Figure 9B:
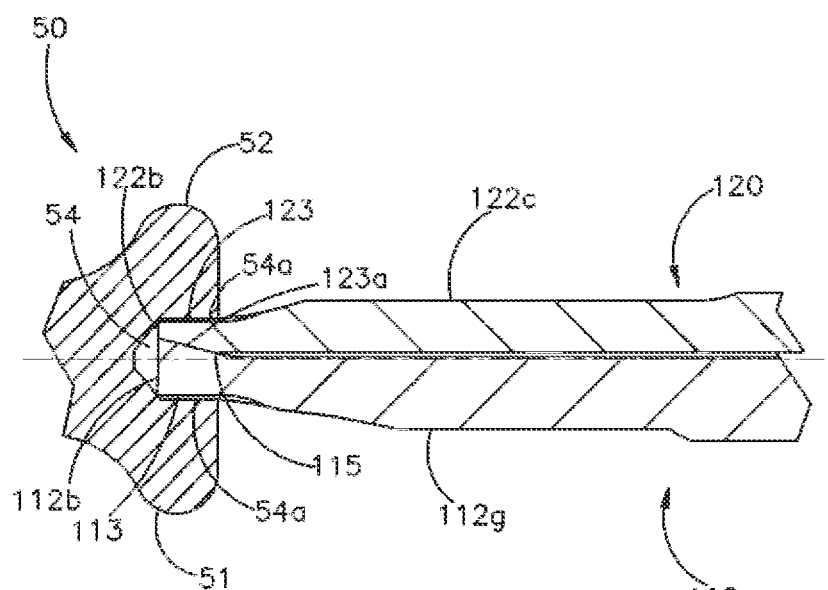
FIG. 9B is a sectional elevation view of the interlock driving instrument illustrated in FIG. 9A inserted into the head of the bone anchor, with the interlock driving instrument in a releasably locked configuration.

It is preferable to insert the driving tips 113 and 123 into the driving opening 54 of the bone screw 51 with the locking screwdriver 100 in the fully unlocked configuration. In the fully unlocked configuration, the sliding member 120 is longitudinally translated within the channel 114 such that the sliding member 120 lies flat against the bottom surface 114a of the channel 114 and the sloped surface 123a of the driving tip 123 lies at the bottom of the sloped surface 115 where the sloped surface 115 transitions to the bottom surface 114a of the channel 114, as illustrated in FIG. 9A. It should be appreciated that the driving tips 113 and 123 may still be insertable into the driving opening 54 of the bone screw 51 when the locking screw driver 100 is in a partially unlocked configuration, for instance when the sloped surface 123a of the driving tip 123 has been longitudinally translated along the sloped surface 115 a short distance.

With the locking screwdriver 100 in the partially or fully unlocked configuration, the driving tips 113 and 123 are inserted into the driving opening 54 of the bone screw 51. With the driving tips 113 and 123 inserted into the driving opening 54, the locking screw driver 100 is then operated to the releasably locked configuration. The locking screwdriver 100 can be operated to the releasably locked configuration by rotating the knob 132 of the actuator 130 about the shaft 110 in a direction that causes the threads 133a of the knob 132 to engage the complimentary threads 119 of the shaft 110 such that the actuator 130 longitudinally translates along the shaft 110 in a direction towards the distal end 112b of the shaft body 112. As the actuator 130 translates, one or more of the annular grooves 136 engage with respective tabs 126 of the sliding member 120, causing the sliding member 120 to concurrently translate with the actuator 130.

As the sliding member 120 translates towards the distal end 112b of the shaft body 112, the driving tip 123, and in particular the sloped surface 123a, rides along the sloped surface 115. As it rides along the sloped surface 123a, the driving tip is 123 is deflected radially upward, causing the upper surface 122c of the driving tip 123 and the outer surface 112g of the driving tip 113 to engage with the respective inner walls 54a of the driving opening 54 of the bone screw 51, imparting outwardly directed forces from the driving tips 113 and 123 to the inner walls 54a of the driving opening 54, and imparting inwardly directed forces from the inner walls 54a of the driving opening 54 to the driving tips 113 and 123 such that the driving opening 54 becomes locked in place on the driving tips 113 and 123. The bone screw 51 can then be driven into or backed out of the underlying structure. When the bone screw 51 has been fully driven or removed, the actuator 130 can be operated to operate the locking screwdriver 100 to the unlocked configuration, wherein the driving tips 113 and 123 can be removed from the driving opening 54 of the bone screw 51.

Figure 10A:
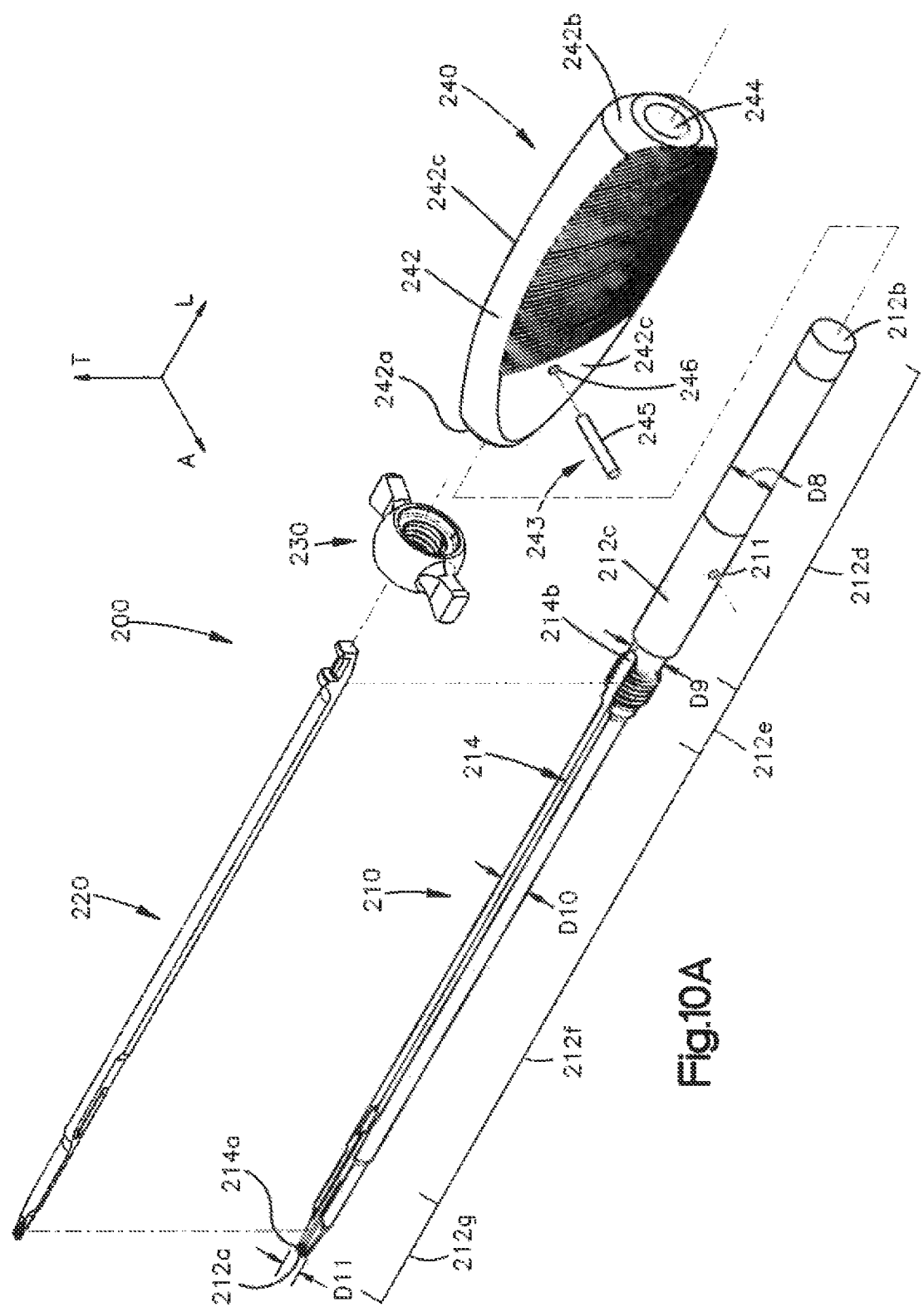
FIG. 10A is an exploded perspective view of the interlock driving instrument constructed in accordance with another alternative embodiment.
Figure 13:
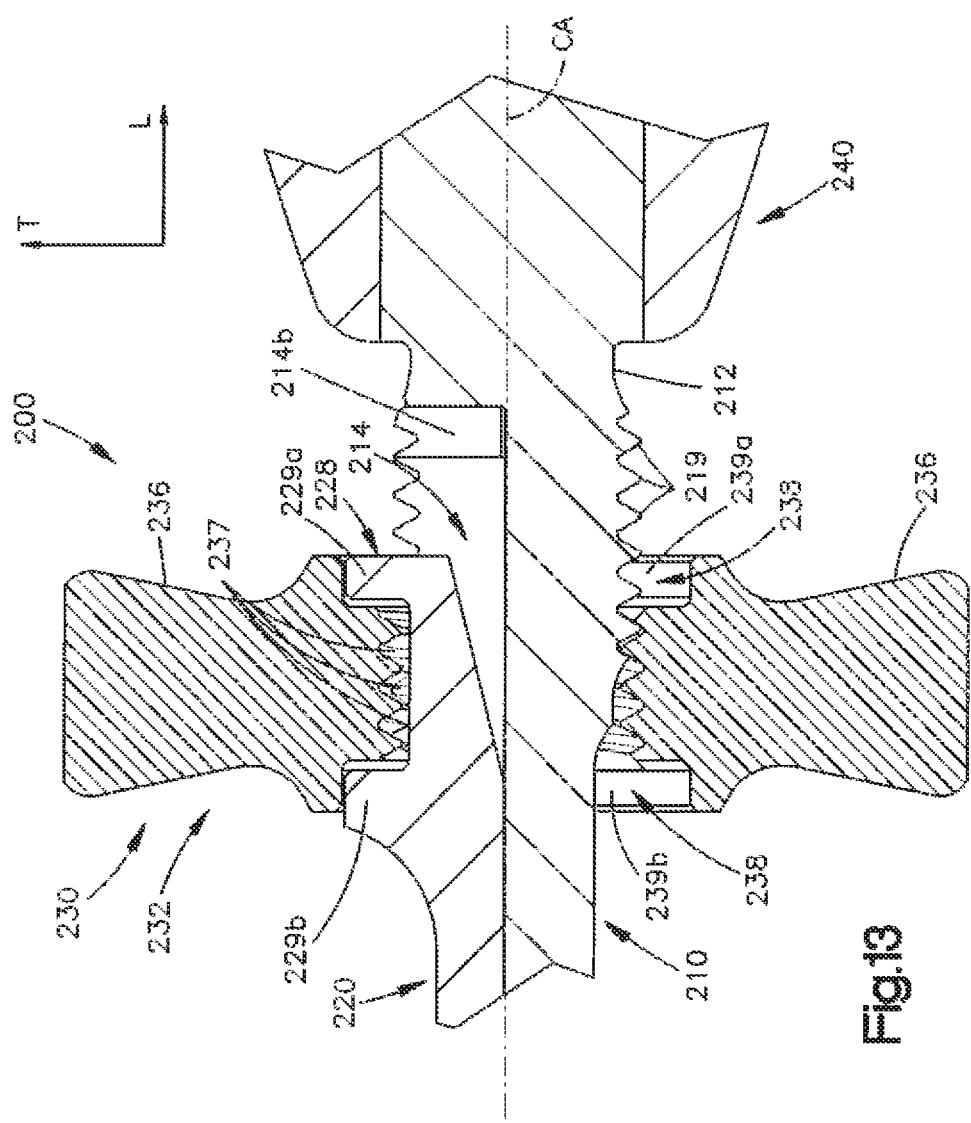
FIG. 13 is a side section view of the actuator component and portions of the shaft and sliding member components illustrated in FIG. 10A.

Referring now to FIGS. 10A-C, a locking screwdriver 200 can be constructed in accordance with another alternative embodiment. The locking screwdriver can be configured to drive a bone anchor 50, such as bone screw 51, into bone. In accordance with the illustrated embodiment, the locking screwdriver 200 can include a number of components, such as a shaft 210 that defines a first guide member, a sliding member 220 that defines a second guide member configured to engage the first guide member so as to direct the sliding member 220 to translate along the shaft 210, an actuator 230 operatively coupled to the shaft 210 and the sliding member 220 and configured to translate the sliding member 220 along the shaft 210, and a handle 240 disposed on an end of the shaft 210. The various components of the locking screwdriver 200 can be made of any suitable material, for instance commercially pure titanium, titanium alloy such as TAN, stainless steel, phenolic reinforced linen, silicon, Radel®, ultra-high-molecular-weight polyethylene (UHMW), and the like.

In accordance with the illustrated embodiment, the shaft 210 includes a shaft body 212 that defines a first end which can define a distal end 212a and further defines an opposed second end that can define a proximal end 212b that is spaced from the distal end 212a along a first direction that can be, for instance, the longitudinal direction L. The shaft body 212 can have any shape as desired, for instance the illustrated generally cylindrically shaped shaft body that is elongate along the first direction and defines a circumferential outer surface 212c. The shaft body 212 can define different cross-sectional dimensions at particular locations along the length of the shaft as defined by the distal end 212a and the proximal end 212b. For example, the shaft body 212 can be constructed with at least one, such as a plurality of longitudinally extending sections, each section having at least one cross-sectional dimension, such as a diameter, that is different than respective cross-sectional dimensions of others of the sections of the shaft body 212.

In accordance with the illustrated embodiment, the shaft body 212 can have a plurality of longitudinal sections, each section having at least one cross-sectional dimension that is different than at least one cross-sectional dimension of other sections of the plurality. The illustrated shaft body 212 has a plurality of sections including a first or grip section 212d, a second or actuator section 212e, a third or intermediate section 212f, and a fourth or tip section 212g. The grip section 212d extends from the proximal end 212b of the shaft body 212 toward the distal end 212a and has a first cross-sectional dimension or diameter D8. The actuator section 212e extends from a distal end of the grip section 212d toward the distal end 212a of the shaft 210 and has a second cross-sectional dimension or diameter D9 that is smaller than the first diameter D8. At least a portion of the outer surface 212c of the shaft body 212 in actuator section 212e can be configured to operably engage with the actuator 230, as described in more detail below. The intermediate section 212f extends from a distal end of the actuator section 212e toward the distal end 212a of the shaft 210 and has a third cross-sectional dimension or diameter D10 that is smaller than both the first diameter D8 and the second diameter D9.

Figure 16A:
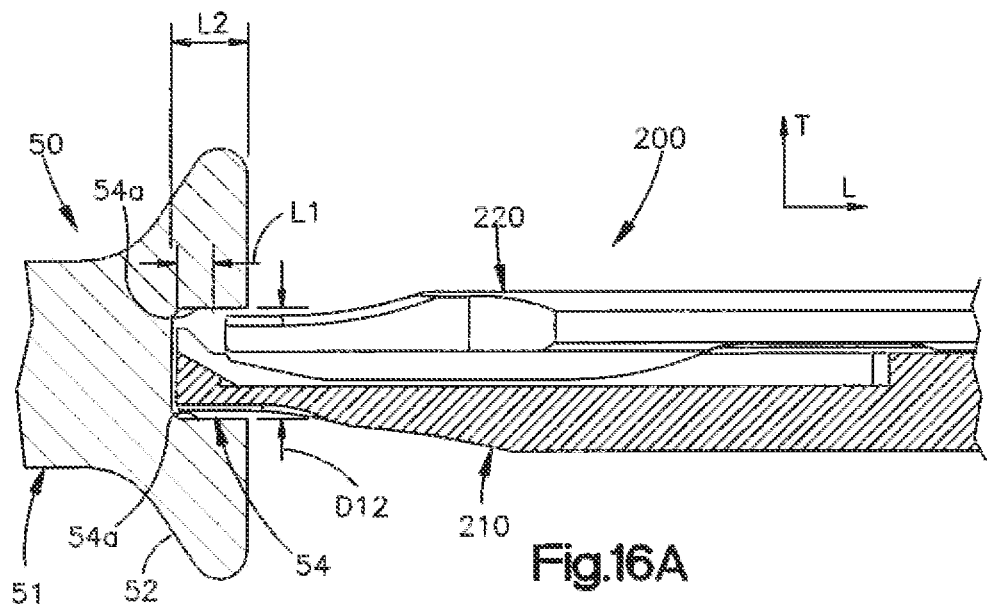
FIG. 16A is a side elevation, partial section view of a portion of the interlock driving instrument illustrated in FIG. 10A, with the instrument inserted into a driving opening in a bone anchor and the sliding member operated into a retracted position in a driving opening of a bone anchor.
Figure 16B:
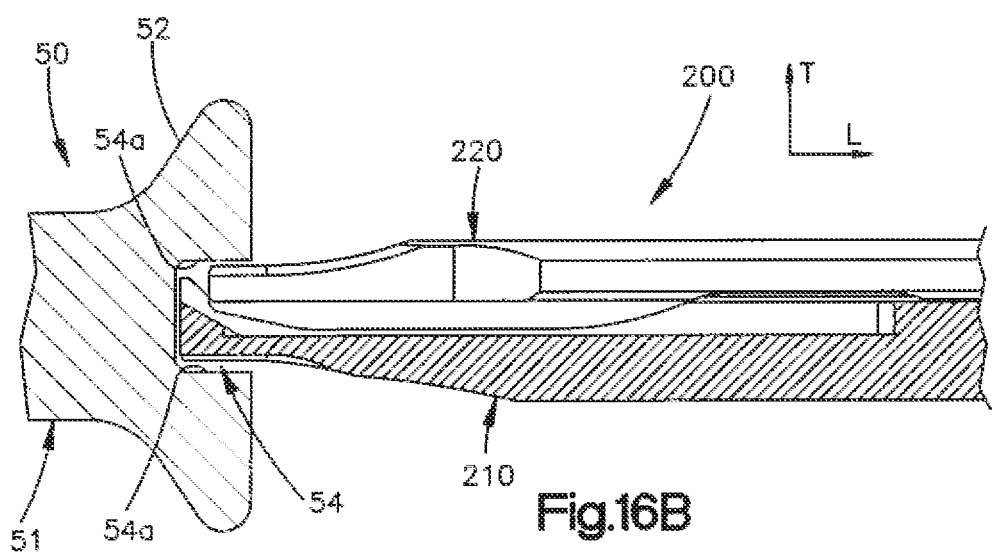
FIG. 16B is a side elevation, partial section view of the portion of the interlock driving instrument illustrated in FIG. 16A, with the sliding member operated into a partially retracted position in the driving opening of the bone anchor.
Figure 16C:
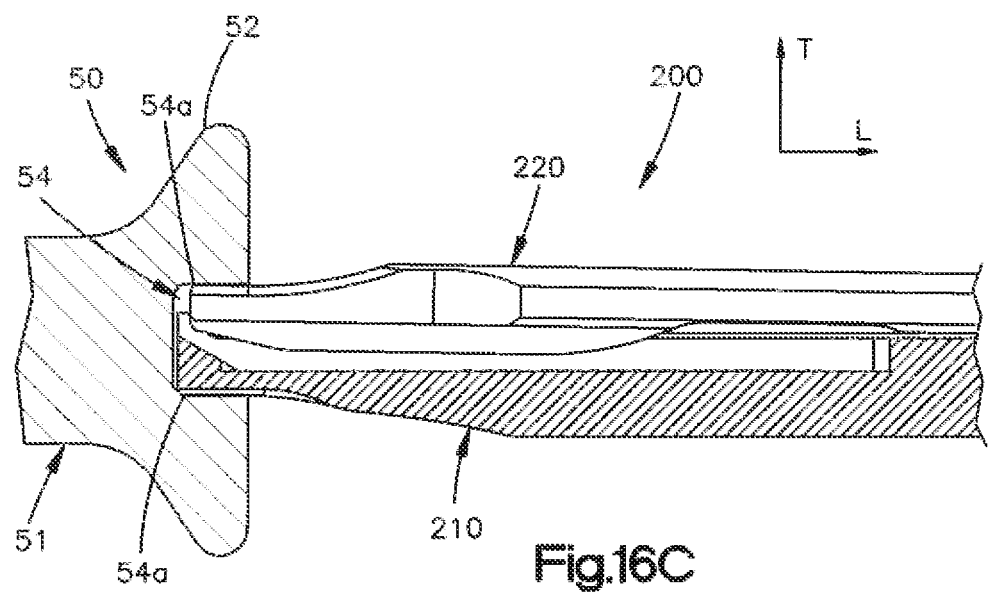
FIG. 16C is a side elevation, partial section view of the portion of the interlock driving instrument illustrated in FIG. 16A, with the sliding member operated into the releasably locked position in the driving opening of the bone anchor.

The tip section 212g extends from a distal end of the intermediate section 212f to the distal end 212a of the shaft 210 and has a cross-sectional dimension that is tapered between the third diameter D10 at a proximal end of the tip section 212g and a fourth cross-sectional dimension or diameter D11 at the distal end 212a of the shaft 210 that is smaller than each of the first diameter D8, the second diameter D9, and the third diameter D10. At least a portion of the tip section 212g, such as the distal end 212a of the shaft 210, can be configured to be received by a driving opening 54 of a complementary bone anchor 50. For instance, in accordance with the illustrated embodiment, the distal end 212a of the shaft can be configured such that the diameter D11 is smaller than a cross-sectional dimension of the driving opening 54 of the bone anchor 50 (see FIG. 16A). It should be appreciated that the shaft 210 is not limited to the illustrated sections or the cross-sectional dimensions of the those sections relative to one another, and that the shaft 210 can alternatively be constructed with any other suitable number of sections having respective cross-sectional dimensions that are the same or different than the respective cross-sectional dimensions of the other sections, as desired.

The grip section 212d of the shaft body 212 can be configured to have a gripping element, such as the handle 240, disposed thereon. For example, in accordance with the illustrated embodiment, the handle 240 includes a handle body 242 that defines a proximal end 242b, an opposed distal end 242a that is spaced from the proximal end 242b along the first direction, and opposed sides 242c spaced apart from one another along a second direction that extends substantially perpendicular to the first direction and can be, for instance, the lateral direction A. The handle body 242 can define a bore 244 that extends at least partially into, such as through the handle body 242 along the first direction, the bore 244 configured to receive the grip section 212d of the shaft body 212 when the handle 240 is disposed onto the shaft 210. Once the handle 240 is disposed onto the shaft 210, the handle 240 can be one or both of affixed to the shaft 210 and oriented relative to the shaft 210, for instance with the use of an attachment member 243, such as a pin 245. In accordance with the illustrated embodiment, the grip section 212d can define a bore 211 that extends at least partially into, such as through the shaft body 212 along the second direction, the bore 211 sized to receive the pin 245 in press fit engagement. The handle can define a second bore 246 that extends at least partially into, such as through the handle body 242 along the second direction, the bore 246 sized to receive the pin 245 in press fit engagement. When the handle 240 is disposed onto and oriented properly relative to the shaft 210, the bore 211 will align with the bore 246, and the pin 245 can be inserted into the bores 211 and 246, thereby securing the handle 240 in the properly oriented position relative to the shaft 210.

At least a portion of the handle can be configured to enhance the ease with which the handle 240, and thus the locking screwdriver 200, can be gripped and manipulated during use. For instance, at least one, such as each of the opposed sides 242c of the handle body 242 can define a respective textured portion 247. In accordance with the illustrated embodiment, each of the opposed sides 242c of the handle body 242 defines a respective textured portion 247 comprising a plurality of grooves 248 defined adjacent to one another, the grooves 248 extending along a direction that is angularly offset relative to the first direction. The direction along which the grooves 248 extend on a first one of the opposed sides 242c of the handle 240 can be the same or different than the direction along which the grooves 248 extend on the other of the opposed sides 242c. It should be appreciated that the locking screw driver is not limited to the illustrated handle geometry or attachment member, and that the locking screwdriver 200 can be one or both of alternatively constructed with a different handle body geometry and affixed to the shaft 210 using a different attachment member. For instance, the grip section 212d of the shaft could be configured similarly to the grip section 12c described above, such that the handle 40 can be affixed to the locking screwdriver 200.

Referring now to FIGS. 10A-C and 11A-D, the shaft 210 can include at least one guide member configured to engage a complementary guide member defined by the sliding member 220 so as to direct the sliding member 220 to translate along the shaft 210. In accordance with the illustrated embodiment, the shaft body 212 defines a first guide member in the form of a channel 214 configured to receive at least a portion of the sliding member 220, such that the sliding member 220 can translate in the channel 214 along the first direction. The channel 214 can extend from the distal end 212a of the shaft 210 toward the proximal end 212b along the first direction. For instance, in accordance with the illustrated embodiment, the channel 214 can extend between a distal end 214a and an opposed proximal end 214b that is spaced apart from the distal end 214a along the first direction. The illustrated channel 214 extends from the distal end 214a, disposed substantially at the distal end 212a of the shaft 210, through the tip section 212g and the intermediate section 212f of the shaft body 212, and extends at least partially into the actuator section 212e, to the proximal end 214b. The illustrated channel 214 extends downward, or inward into the shaft body 212 along a third direction that extends substantially perpendicular to both the first and second directions and can be, for instance, the transverse direction T.

The channel 214 can be configured having any geometry suitable to allow the sliding member 220 to translate in the channel 214 along the first direction. For instance, in accordance with the illustrated embodiment, the channel 214 is configured as an open channel having a substantially rectangular cross section that defines a bottom surface 214c along which the sliding member 220 translates, and opposing side surfaces 214d that extend upward from the bottom surface 214c along the third direction to respective upper edges 214e defined at the intersection of the respective side surfaces 214d and the outer surface 212c of the shaft body 212. The illustrated channel 214 defines a width W5 along the second direction that is smaller than the diameters D9 and D10 of the actuator section 212e and the intermediate section 212f of the shaft body 212, respectively. It should be appreciated that the channel 214 is not limited to the illustrated cross-sectional geometry, and that the channel 214 can alternatively define any other suitable cross-sectional geometry as desired, for instance to allow an alternatively constructed sliding member to translate in the channel along the first direction.

The shaft 210 can include at least one, such as a plurality, for instance a pair, of ramps 213 disposed proximate the distal end 212a of the shaft 210, the ramps 213 configured to cause at least a portion of the sliding member 220 to be displaced radially outward within the driving opening 54 of a bone anchor 50, as described in more detail below. For example, in accordance with the illustrated embodiment, the shaft 210 can include a pair of ramps 213 that extend outwardly from the bottom surface 214c of the channel 214 along the third direction, the ramps 213 spaced apart from each other along the second direction so as to define a gap therebetween. In accordance with the illustrated embodiment, the ramps 213 can be integral with the shaft body 212. Alternatively, the ramps 213 can be constructed separately from the shaft body 212 and subsequently affixed thereto.

Each ramp 213 can define a sloped surface 213a that is angularly offset relative to the first direction, such that when corresponding portions of the sliding member 220 ride along the respective sloped surfaces 213 a of the ramps 213, as described in more detail below, at least a portion of the sliding member 220 is displaced radially outward relative to the bottom surface 214c of the channel 214. The sloped surfaces 213a can flare outward along the transverse direction T as they extend along a direction that is defined from the proximal end 212b to the distal end 212a. For instance, the sloped surfaces 213a can define any angle with respect to the longitudinal direction L as desired. In accordance with one embodiment, the sloped surfaces 231 define an angle within the range of 15 degrees and 75 degrees, such as approximately 45 degrees. Each ramp 213 can further define a respective transition location 213b where the respective sloped surface 213a of each ramp 213 intersects with, or meets the channel 214. For instance, in accordance with the illustrated embodiment, the transition location 213b of each ramp 213 is spaced from the distal end 212a of the shaft 210 a distance L1 that is shorter than a depth L2 of the driving opening 54 of the bone anchor 50 (see FIG. 16A). Thus, it can be said that the respective transition location 213b of each of the plurality of ramps 213 is equally spaced from the distal end 212a of the shaft 210 along the first direction. Further, in accordance with the illustrated embodiment the sloped surface 213a of each ramp 213 is straight between a respective top end 213c of each ramp and the corresponding transition location 213b of each ramp 213.

It should be appreciated that the ramps 213 are not limited to the illustrated sloped surfaces 213a, and that the sloped surface 213a of at least one, such as each of the ramps 213 can be alternatively configured using any other surface geometry as desired. For instance, the sloped surface 213a of at least one, such as each of the ramps 213 can be at least partially curved between the respective top end 213c of the ramp 213 and the respective transition location 213b of the ramp 213. It should further be appreciated that the transition location 213b of each of the plurality of ramps 213 need not be equally spaced from the distal end 212a of the shaft 210. For instance, the transition location 213b of at least a first one of the plurality of ramps 213 can be spaced further or nearer the distal end 212a of the shaft 210 than the transition location 213b of a second one of the plurality of ramps 213, such that the first one of the plurality of ramps 213 defines a sloped surface 213a that is angularly offset at an angle that is shallower or steeper relative to the first direction than the angle at which the sloped surface 213a of the second of the plurality of ramps 213 is angularly offset relative to the first direction.

The shaft 210 can further include at least one, such as a plurality of retaining members 215 configured to retain the sliding member 220 in the channel 214. For example, the shaft 210 can include a plurality of retaining members 215 that extend inwardly relative to the opposed sides 214d of the channel 214, so as to capture at least a portion of the sliding member 220. The retaining members 215 can be configured to retain the sliding member 220 in the channel 214 such that the sliding member 220 does not protrude beyond a profile of the shaft 210, for example a profile defined by the outer surface 212c of the shaft body 212. In accordance with the illustrated embodiment, the shaft 210 includes a pair of retaining members 215 that include laterally opposed arced projections 216, each arced projection 216 comprising at least an upper portion 216a that extends upward and inward from a respective upper edge 214e of a respective one of the opposed sides 214d of the channel 214. The upper portions 216a of the arced projections 216 are configured to capture and a respective portion of the sliding member 220 in the channel 214 and thus retain the sliding member 220 in the channel 114, as described in more detail below. In accordance with the illustrated embodiment, the upper portions 216a of the arced projections 216 can extend upward relative to the upper edges 214e of the channel 214 and inward relative to the opposed sides 214d of the channel 214, between inner ends 216c disposed substantially at respective ones of the upper edges 214e of the channel 214, and opposed outer ends 216b that are spaced inward along the second direction from the respective opposed sides 214d of the channel 214. The respective outer ends 216b of the upper potions 216a of the arced projections 216 can be spaced apart from each other such that a gap 216d is defined between the outer ends 216b, the gap 216d having a width W6 along the second direction that is shorter than the width W5 of the channel 214.

Each arced projection 216 can further comprise a lower portion 216e that extends downward relative to the outer end 216b of the upper portion 216a and inward relative to the respective opposed side 214d of the channel 214. The upper and lower portions 216a and 216e of each arced projection can define a respective groove 217 that is spaced inward from the respective opposed side 214d of the channel 214, the groove 217 configured to slidably receive and retain at least a portion of the sliding member 220, as described in more detail below. The arced protrusions 216 on each of the opposed sides 214d of the channel 214 can be substantially identically constructed, such that the arced protrusions 216 define a pair of laterally opposed grooves 217 that face one another along the second direction. It should be appreciated that the shaft 210 is not limited to the illustrated retaining members 215, and that the shaft 210 can alternatively be constructed with any other suitable retaining members as desired. In accordance with the illustrated embodiment, the retaining members 215 can be integral with the shaft body 212. Alternatively, the retaining members 215 can be constructed separately from the shaft body 212 and subsequently affixed thereto.

Referring now to FIGS. 10A-B and 12A-E, in accordance with the illustrated embodiment, the sliding member 220 includes a sliding member body, or sliding body 222 that extends between a first end 222a, which can define a distal end, and an opposed second end 222b, which can define a proximal end, that is spaced from the first end 222a along the first direction, and opposed sides 222c that are spaced from each other along the second direction. The sliding member 220 can include at least one guide member configured to engage a complementary guide member defined by the shaft 210 so as to direct the sliding member 220 to translate along the shaft 210 and onto at least one, such as each of the plurality of ramps 213. For example, the sliding member 220 can define a second guide member configured to engage with a first guide member of the shaft 210. In accordance with the illustrated embodiment, the shaft body 222 defines a guide member in the form of a lower, or sliding surface 222d configured to translate along the bottom surface 214c of the channel 214 and an opposed upper, or outer surface 222e that is spaced from the sliding surface 222d along the third direction. The sliding body 222 can have any shape as desired, for instance the illustrated sliding body 222 having a cross-sectional profile with a generally rectangular lower portion defined by the opposed sides 222c and the sliding surface 222d, and a curved upper portion defined by the outer surface 222e that is configured to substantially match the profile of the outer surface 212c of the shaft body 212 when the sliding member 220 is disposed in the channel 214.

It should be appreciated that the locking screwdriver 200 is not limited to the illustrated guide members, such as the first guide member in the form of channel 214 and the second guide member in the form of the sliding surface 212d, and the that locking screwdriver 200 can alternatively include any other suitable guide members as desired. For example, in accordance with an alternative embodiment the shaft 210 can include a first guide member that extends outward from the outer surface 212c of the shaft body 212, the first guide member configured to be receive in a complementary second guide member that extends into the outer surface 222e of the sliding body 222.

At least a portion of the sliding member 220, such as the first end 222a, can be configured to be received by a driving opening 54 of a complementary bone anchor 50. Furthermore, the first end 222a of the sliding member 220 can be configured to be disposed in the driving opening 54 of a bone anchor 50 concurrently with the distal end 212a of the shaft 210, as described in more detail below.

The sliding body 222 can have a width W7 along the second direction, for instance defined by the opposed sides 222c, the width W7 approximately equal to but shorter than the width W5 of the channel 214, such that when the sliding member 220 is disposed in the channel 214, the sliding member 220 can freely move, or translate along the first direction within the channel 214. The sliding member 220 can be constructed such that the opposed sides 222c of the sliding body 222 are not spaced further apart relative to another than the width W7. The sliding member 220 can have a length along the first direction, for instance as defined by the first and second ends 222a and 222b of the sliding body 222, respectively, that is shorter than a length of the channel 214 along the first direction, for instance as defined by the distal and proximal ends 214a and 214b of the channel 214, respectively. For example, in accordance with the illustrated embodiment, the sliding member 220 can be constructed such that when the sliding member 220 is disposed in the channel 214 with the second end 222b of the sliding member 220 disposed substantially at the proximal end 214b of the channel 214, the first end 222a of the sliding member 220 will be disposed proximally from the distal end 212a of the shaft 210 and, more particularly, disposed proximally relative to the respective transition locations 213b of at least one, such as all of the plurality or ramps 213.

The locking screwdriver 200 can be operated between a retracted configuration in which the distal end 212a of the shaft 210 and the first end 222a of the sliding member 220 can be freely inserted into or removed from the driving opening 54 of a bone anchor 50, and a releasably locked configuration in which the distal end 212a of the shaft 210 and the first end 222a of the sliding member 220 are releasably locked within the driving opening 54 of the bone anchor 50. Operating the locking screwdriver 200 from the retracted configuration to the releasably locked configuration can cause the sliding member 220 to be operated from a first, or retracted position relative to the shaft 210 to a second, or releasably locked position within the driving opening 54 of a bone anchor 50.

The sliding member 220 can be operated from the retracted position to the releasably locked position by operating the actuator 230. When the actuator 230 is operated, the actuator 230 can apply a force to the sliding member 220 that biases the sliding member 220 to translate along the shaft 210 in a forward direction toward the distal end 212a of shaft 210 that can be, for instance, the longitudinal direction L, to the releasably locked position. The first end 222a of the sliding member 220 can be configured to ride along the ramps 213 when the sliding member 220 translates form the retracted position to the releasably locked position, thereby causing at least the first end 222a of the sliding member 220 to be displaced radially outward within the driving opening 54 of the bone anchor 50, releasably locking the distal end 212a of the shaft 210 and the first end 222a of the sliding member 220 within the driving opening 54 of the bone anchor 50. Stated differently, the locking screwdriver 200 is releasably locked to the bone anchor 50 when the sliding member 220 and the distal end 212a of the shaft 210 are disposed in the driving opening 54 and the sliding member 220 is in the releasably locked position.

The first end 222a of the sliding member 220 can define at least one, such as a plurality of riding surfaces 223, each riding surface configured to ride along a respective one of the plurality of ramps 213, for instance when the locking screwdriver 200 is operated from the retracted configuration to the releasably locked configuration. In accordance with the illustrated embodiment, the first end 222a of the sliding member 220 defines a pair of riding surfaces 223 spaced apart from one another along the second direction. The riding surfaces 223 are angularly offset relative to the first direction. The illustrated riding surfaces 223 are angularly offset relative to the first direction through an angle that is substantially equal to the angle at which the sloped surfaces 213a of the ramps are angularly offset relative to the first direction. However it should be appreciated that at least one, such as each of the plurality of riding surfaces 223 can be angularly offset relative to the first direction at respective angles that are shallower or steeper than the angle at which corresponding ones of the sloped surfaces 213a of the ramps are angularly offset relative to the first direction.

The sliding member 220 can include at least one, such as a plurality of structural members configured to enhance one or more structural characteristics of the sliding member 220. For example, the at least one structural member can act to increase the amount of rotational force that can be safely imparted to the sliding member 220. In accordance with the illustrated embodiment, the sliding member 220 can include at least one structural member, for instance a projection 224 supported by the sliding member 220 that extends outward from the sliding surface 222d of the sliding body 222. The projection 224 can extend between a first, or distal end 224a, an opposed second, or proximal end 224b that is spaced from the distal end 224a along the first direction, and opposed sides 224c that are spaced apart from each other along the second direction. The illustrated projection 224 can extend from the first end 222a of the sliding member 220 toward the second end 222b along the first direction. For example, in accordance with the illustrated embodiment, the projection 224 can extend along a centerline C2 of the sliding member 220 that extends substantially parallel relative to the first direction, and equidistantly between the opposed sides 222c of the sliding body 222. Furthermore, the illustrated projection 224 extends outward, or downward from the sliding surface 222d along the third direction. In accordance with the illustrated embodiment, the sliding body 222 defines a pair of riding surfaces 223, each riding surface 223 disposed adjacent a respective one of the opposed sides 224c of the projection 224.

Referring now to FIGS. 11A-D and 12A-E, the shaft 210 can define a groove 218 sized to receive the projection 224. In accordance with the illustrated embodiment, the groove 218 can extend into the bottom surface 214c of the channel 214 along the third direction. The groove 218 can extend between a first, or distal end 218a, an opposed second, or proximal end 218b that is spaced from the distal end 218a along the first direction, and can define opposed sides 218c that are spaced apart from each other along the second direction. The illustrated groove 218 extends from the distal end 212a of the shaft 210 toward the proximal end 212b along a centerline C1 of the shaft 210 that extends substantially parallel relative to the first direction. Furthermore, the illustrated groove 218 extends into the shaft body 212 along the third direction. In accordance with the illustrated embodiment, the plurality of ramps 213 comprises a pair of ramps 213, each ramp 213 of the pair of ramps 213 disposed adjacent a respective one of the opposed sides 218c of the groove 218.

The projection 224 can be configured to be received in the groove 218 such that the projection 224 can translate within the groove 218 when the sliding member 220 is operated from the retracted position to the releasably locked position. For example, in accordance with the illustrated embodiment, the groove 218 can define a length along the first direction, for instance as defined by the distal and proximal ends 218a and 218b, that is longer than the length of the projection 224 along the first direction, for instance as defined by the distal and proximal ends 224a and 224b. One or both of the groove 218 and the projection 224 can further be configured such that the projection 224 will not make contact with the groove 218 when the sliding member 220 is translated along the first direction relative to the shaft 210. For example, in accordance with the illustrated embodiment, the groove 218 defines a sloped surface 218d that is angularly offset relative to the first direction and the projection 224 defines a sloped surface 224d that is angularly offset relative to the first direction. During operation of the locking screwdriver 200 from the retracted position to the releasably locked position, the projection 224 will translate distally in the groove 218 such that the sloped surface 224d of the projection 224 does not make contact with the sloped surface 218d of the groove 218.

It should be appreciated that the locking screwdriver 200 is not limited to the illustrated projection 224 and groove 218, and that the locking screwdriver 200 can alternatively be constructed with any other suitable configuration of projections 224 and grooves 218. For instance, in accordance with an alternative embodiment the locking screwdriver 200 can alternatively be constructed with a plurality of projections 224 and a corresponding plurality of grooves 218. In accordance with another alternative embodiment, the projection 224 can extend outward from the sliding surface 222d of the sliding body 222 along a direction that is angularly offset relative to the third direction. Of course the groove 218 can be alternatively configured to accommodate translation of the projection 224 in the groove. In accordance with still another alternative embodiment, the projection 224 can extend along a direction that is substantially parallel with the first direction, but laterally offset relative to the centerline C2 of the sliding body 222. Of course the groove 218 can similarly be laterally offset relative to the centerline C1 of the shaft body 212 in so as to accommodate translation of the projection 224 in the groove 218. It should further be appreciated that one or both of the projection 224 and the groove 218 of the sliding member 220 and the shaft 210, respectively, can be alternatively constructed utilizing any combination of the above-described alternative embodiments, as desired.

With continuing reference to FIGS. 11A-D and 12A-E, at least a portion of the sliding member 220 can be configured to cooperate with the retaining members 215 of the shaft 210, and in particular the arced protrusions 216. For example, the sliding body 222 can define a retaining section 225 that has a width W8 along the second direction that is approximately equal to but shorter than the width W6 of the gap 216d between the outer ends 216b of the arced projections 216, such that at least a portion of the retaining section 225 can be disposed through the gap 216d between the arced projections 216 and into the channel 214. In accordance with the illustrated embodiment, the retaining section 225 extends between a first, or distal end 225a located proximally relative to the first end 222a of the sliding member 220, a second, or proximal end 225b that is spaced proximally from the distal end 225a along the first direction, and opposed sides 225c that are spaced apart along the second direction, inwardly from the opposed sides 222c.

The sliding member 220 can include at least one, such as a plurality of retaining members 215 configured to retain the sliding member 220 in the channel 214. The retaining members 215 of the sliding member 220 can be configured to cooperate with the retaining members 215 of the shaft 210. For example, in accordance with the illustrated embodiment, the sliding member 220 includes a plurality of retaining members 215 in the form of a pair of retention wings 226 defined in the retaining section 225 of the sliding body 222. Each retention wing 226 can extend between a first, or distal end 226a that can be disposed substantially at the distal end 225a of the retaining section 225 and an opposed second, or proximal end 226b that is spaced proximally from the distal end 226a along the first direction, and can extend outward from a respective one of the opposed sides 225c, along the second direction, to an outer side 226c. In accordance with the illustrated embodiment, the outer side 226c of each of the retention wings 226 can be substantially coincident with a corresponding one of the opposed side 222c of the sliding body 222.

The proximal end 226b of each retention wing 226 can be located at a distance from the distal end 225a of the retaining section 225 such that a length L3 along the first direction, defined by the proximal end 226b of each retention wing 226 and the proximal end 225b of the retaining section 225 is approximately equal to but longer than a length L4 along the first direction of each of the arced projections 216, such that at least the portion of the retaining section 225 that extends from the proximal end 226b of each retention wing 226 to the proximal end 225b can be disposed past the arced projections 216 and into the channel 214. Each retention wings 226 can be configured such that when the sliding member 220 is disposed into the channel 214, the retention wing 226 can be at least partially received in nesting engagement by a corresponding one of the arced projections 216, and in particular the groove 217 defined by the corresponding one of the arced projections 216. For example, in accordance with the illustrated embodiment, the cross-sectional profile of each retention wing 226 can be configured such that each retention wing 226 can be received by a corresponding one of the grooves 217 defined by the arced projections 216. During operation of the locking screwdriver 200 between the retracted and releasably locked configurations, as described in more detail below, the retention wings 226 can engage within the grooves 217, such that engagement between the pair of retention wings 226 and the pair of arced projections 216 retains the sliding member 220 in the channel 214. Each retention wing 226 can have a length along the first direction, for instance as defined by the distal and proximal ends 226a and 226b, sufficient to maintain the nested engagement of each retention wing 226 within a corresponding groove 217 defined by a respective one of the arced projections 216 as the locking screwdriver 200 is operated between the retracted and releasably locked configurations.

Referring now to FIGS. 10A-B and 12A-E, the second end 222b of the sliding member 220 can be configured to be operatively coupled to the actuator 230, such that operation of the actuator 230 will cause the sliding member to translate between the retracted and releasably locked positions. For example, the sliding member 220 can include at least one, such as a plurality of coupling members 228, the coupling members 228 configured to be received by the actuator 230. In accordance with the illustrated embodiment, the sliding member 220 includes a pair coupling members 228 in the form of tabs 229 that extend outward from the sliding member 220 proximate the second end 222b of the sliding member 220 along the third direction. In particular, each of the pair of tabs 229 can extend transversely upward from the outer surface 222e of the sliding body 222 along the third direction. A first tab 229a of the pair of tabs 229 can be disposed substantially at the second end 222b of the sliding member 220. A second tab 229b of the pair of tabs 229 can be disposed distally relative to the first tab 229a, such that the first and second tabs 229a and 229b of the pair of tabs 229 are spaced apart from one another along the first direction.

Referring now to FIGS. 13 and 14A-C, the sliding member 220 can be operatively coupled to the actuator 230, and the actuator 230 can be operatively coupled to the shaft 210, such that when the actuator 230 is operated, the sliding member 220 is translated within the channel 214 along the first direction. For example, in accordance with the illustrated embodiment, the sliding member 220 can be captively coupled to the actuator 230 and the actuator 230 can be in threaded engagement with the shaft 210.

The actuator 230 can be provided as a threaded knob 232. In accordance with the illustrated embodiment, the knob 232 includes a knob body 234 that defines a first, or distal end 234a, an opposed second, or proximal end 234b that is spaced from the distal end 234a along the first direction, and a circumferential outer surface 234c. The knob body 234 can have any shape as desired, for instance the illustrated generally annular shaped knob body 234. The knob 232 can include at least one, such as a plurality of gripping elements 235. For example, in accordance with the illustrated embodiment, the knob 232 includes a pair of gripping elements in the form of a pair of tabs 236 that extend outward from the outer surface 234c of the knob body 234. The illustrated tabs 236 extend outward from laterally opposed sides of the knob body 234 along the second direction.

The knob body 234 can define a bore 233 that extends through the knob body 234 along a central axis CA that extends substantially parallel to the first direction. The bore 233 can define an inner surface 233a configured to operably engage with the shaft 210. For example, in accordance with the illustrated embodiment, a first plurality of helical threads 237 can be defined along the inner surface 233a. A complementary second plurality of threads 219 can be defined along at least a portion of the outer surface 212c of the shaft 210, the second plurality of threads 219 configured to engage with the first plurality of threads 237 when the actuator 230 is operated. In accordance with the illustrated embodiment, the second plurality of threads 219 can extend outward from the outer surface 212c of the shaft body 212 along at least a portion of the actuator section 212e. It should be appreciated that locking screwdriver 200, and in particular the shaft 210, is not limited to the illustrated location of the second plurality of threads 219, and thus is not limited to the illustrated location along the shaft 210 where the actuator is operably coupled to shaft 210. For example, the shaft 210 can be alternatively constructed with the second plurality of threads 219 located at any other suitable location along the outer surface 212c of the shaft body 212, and thus the location where the actuator 230 can be operably coupled to the shaft 210 can be located at any other suitable location along the shaft 210.

The actuator 230 can define at least one, such as a plurality of coupling interfaces 238, each coupling interface 238 configured to receive a corresponding one of the plurality of coupling members 228, thereby operably coupling the sliding member 220 to the actuator 230 and to the shaft 210. Each coupling interface 238 can be configured to engage with at least one coupling member 228, such that engagement between the coupling interface 238 and the respective at least one coupling member 228 causes the sliding member 220 to translate in the channel 214. For example, in accordance with the illustrated embodiment, the knob body 234 defines a plurality of coupling interfaces 238 in the form of a pair of annular grooves 239 that extend into opposed ends of the knob body 234 along the first direction. In particular, a first annular groove 239a extends into the proximal end 234b of the knob body 234, and a second annular groove 239b extends into the distal end 234a of the knob body 234.

The first annular groove 239a can be configured to receive and captively retain the first tab 229a, and the second annular groove 239b can be configured to receive and captively retain the second tab 229b. Stated differently, each annular groove 239 can be configured to receive a respective one of the pair of tabs 229. The first and second annular grooves 239a and 239b can be configured to allow free rotation of the knob body 234 about the first and second tabs 229a and 229b during operation of the threaded knob 232. Stated differently, when the sliding member 220 is disposed in the channel 214 and the first and second tabs 229a and 229b are disposed in the first and second annular grooves 239a and 239b, respectively, if the knob body 234 is rotated about the central axis CA the first and second tabs 229a and 229b will not rotate concurrently with the knob body 234.

In accordance with the illustrated embodiment, the threaded knob 232 can be operated by applying a rotational force to the knob body 234 about the central axis CA, for instance by applying a rotational force to at least one, such as both of the tabs 236. If a rotational force is applied to the actuator 230 in a first rotation direction about the central axis CA, the first and second pluralities of threads 237 and 219 will engage with one another, and the threaded knob 232 will advance distally in the forward direction along the shaft 210. As the threaded knob 232 advances distally along the shaft 210, the second annular groove 239b will engage with the second tab 229b and apply a force to the second tab 229b that biases the sliding member 220 to translate in the channel 214 in the forward direction toward the distal end 212a of shaft 210.

Contrastingly, if a rotational force is applied to the threaded knob 232 in a second rotation direction about the central axis CA that is substantially opposite the first rotation direction about the central axis CA, the first and second pluralities of threads 237 and 219 will engage with one another, and the threaded knob 232 will advance proximally along the shaft 210 in a rearward direction that can be, for instance, the longitudinal direction L, such that the rearward direction is substantially opposite the forward direction. As the threaded knob 232 advances proximally along the shaft 210, the first annular groove 239a will engage with the first tab 229a and apply a force to the first tab 229a that biases the sliding member 220 to translate in the channel 214 in the rearward direction toward the proximal end 212b of shaft 210. It should further be appreciated that the locking screwdriver 200 is not limited to the illustrated actuator, and in particular the threaded knob 232, and that the locking screwdriver can be alternatively constructed with any other suitable actuator that causes the sliding member 220 to translate in the channel 214. For instance, the actuator 130, and in particular the threaded knob 132, can be utilized with the locking screwdriver 200.

Referring now to FIGS. 15A-D and 16A-C, a portion of one or both of the shaft 210 and the sliding member 220 can include at least one, such as a plurality of driving elements 250 configured to engage with complementary driving elements defined in the driving opening 54 of a complementary bone anchor 50. For instance, in accordance with the illustrated embodiment, the distal end 212a of the shaft 210 defines a first plurality 250a of driving elements 250 in the form of a pair of star drive elements 251 that extend outward from the outer surface 212c of the shaft body 212. In further accordance with the illustrated embodiment, the first end 222a of the sliding member 220 defines a second plurality 250*b* of driving elements 250 in the form of four star drive elements 251 that extend outward from the outer surface 222*e* of the sliding body 222.

The first and second pluralities 250*a* and 250*b* of driving elements 250 can be radially arranged about the respective outer surfaces 212*c* and 222*e* of the shaft body 212 and the sliding body 222 in a configuration that is substantially equivalent to a typical one piece star driving instrument. Accordingly, when the distal end 212*a* of the shaft 210 and the first end 222*a* of the sliding member 220 are locked in the driving opening 54 of a bone anchor 50 that is configured for use with a star driving instrument and a rotational force is applied to the locking screwdriver 200 about the central axis CA, the first and second pluralities 250*a* and 250*b* of driving elements 250 will engage with complementary star drive elements in the driving opening 54 of the bone anchor, thereby transmitting the torque to the bone anchor 50. It should be appreciated that the locking screw driver, and in particular the shaft 210 and the sliding member 220, are not limited to the illustrated first and second pluralities 250*a* and 250*b* of star drive elements, and that one or both of the shaft 210 and the sliding member 220 can alternatively be configured with any other suitable driving elements as desired.

In accordance with a method of operation of the locking screwdriver 200, a bone anchor 50, such as a bone screw 51, can be releasably locked onto the locking screwdriver 200 in preparation for insertion or removal of the bone screw 51 from an underlying structure, such as an underlying bone of a patient. In accordance with the illustrated embodiment, the bone screw 51 can be releasably locked onto the locking screwdriver 200 by inserting the distal end 212*a* of the shaft 210 and the first end 222*a* of the sliding member 220 into the driving opening 54 of the bone screw 51 and operating the locking screwdriver 200 into the releasably locked configuration.

It is preferable to insert the distal end 212*a* of the shaft 210 and the first end 222*a* of the sliding member 220 into the driving opening 54 of the bone screw 51 with the locking screwdriver 200 operated fully into the retracted configuration. When the locking screwdriver 200 is operated fully into the retracted configuration, the sliding member 220 is in the retracted position within the channel 214 such that the sliding surface 222*d* of the sliding body 222 abuts the bottom surface 214*c* of the channel 214, the second end 222*b* of the sliding member 220 is disposed substantially at the proximal end 214*b* of the channel 214, and the first end 222*a* of the sliding member 220 will be disposed proximally from the distal end 212*a* of the shaft 210 and, more particularly, disposed proximally relative to the respective transition locations 213*b* of at least one, such as all of the plurality or ramps 213 (see FIGS. 15A and 16A). Furthermore, when the locking screwdriver 200 is operated completely to the retracted configuration, the projection 224 is disposed in the groove 218 (see FIG. 15D). It should be appreciated that the distal end 212*a* of the shaft 210 and the first end 222*a* of the sliding member 220 can be inserted into the driving opening 54 of the bone screw 51 when the locking screwdriver 200 is operated to an intermediate, or partially retracted configuration, wherein the sliding member 220 is operated into a partially retracted position relative to the shaft 210. For example, the actuator 230 can be operated through a distance about the central axis CA sufficient to cause the sliding member 220 to translate along the forward direction in the channel 214 a short distance, such that the locking screwdriver 200 is operated into a partially retracted configuration.

With the locking screwdriver 200 operated to a partially retracted configuration or operated fully into the retracted configuration, the distal end 212*a* of the shaft 210 and the first end 222*a* of the sliding member 220 can be inserted into the driving opening 54 of the bone screw 51. With the distal end 212*a* of the shaft 210 and the first end 222*a* of the sliding member 220 inserted into the driving opening 54 of the bone screw 51, the locking screw driver can be operated from the partially retracted configuration or the retracted configuration to the releasably locked configuration, thereby releasably locking the distal end 212*a* of the shaft 210 and the first end 222*a* of the sliding member 220 within the driving opening 54 of the bone screw 51. The locking screwdriver 200 can be operated to the releasably locked configuration by operating the actuator 230, for instance by applying a rotational force to at least one, such as both of the tabs 236 of the threaded knob 232. Applying a rotational force to the actuator 230 in a first rotation direction about the central axis CA causes the first and second pluralities of threads 237 and 219 to engage with one another, and causes the threaded knob 232 to advance distally in the forward direction along the shaft 210. As the threaded knob 232 advances distally along the shaft 210, the second annular groove 239*b* engages with the second tab 229*b*, thereby causing the sliding member 220 to translate in the forward direction in the channel 214 toward the plurality of ramps 213 (see FIGS. 15B and 16B).

As the sliding member 220 translates distally toward the distal end 212*a* of the shaft 210, each of the riding surfaces 223 will ride up along a corresponding sloped surface 213*a* of a respective one of the plurality of ramps 213, causing at least a portion of the sliding member 220, such as the first end 222*a*, to be displaced radially outward within the driving opening 54 of the bone screw 51. As the first end 222*a* of the sliding member 220 is displaced further outward, the locking screwdriver 200 will be operated into the releasably locked configuration, wherein the respective outer surfaces 212*c* and 222*e* of the shaft body 212 and the sliding body 222 are engaged with respective inner walls 54*a* of the driving opening 54 of the bone screw 51 (see FIGS. 15C and 16C). When the outer surfaces 212*c* and 222*e* of the shaft body 212 and the sliding body 222 are engaged with respective inner walls 54*a* of the driving opening 54, outwardly directed forces are imparted to the inner walls 54*a* of the driving opening 54 from the outer surfaces 212*c* and 222*e*. Similarly, inwardly directed forces are imparted to the outer surfaces 212*c* and 222*e* from the inner walls 54*a* of the driving opening 54. The outwardly and inwardly directed forces can create an interference lock between the respective outer surfaces 212*c* and 222*e* of the shaft body 212 and the sliding body 222 and the respective inner walls 54*a* of the driving opening 54 of the bone screw 51, such that the driving opening 54 is releasably locked in place on the distal end 212*a* of the shaft and the first end 222*a* of the sliding member 220.

In accordance with the illustrated embodiment, when the bone screw 51 is releasably locked in place on the distal end 212*a* of the shaft and the first end 222*a* of the sliding member 220, the first and second pluralities 250*a* and 250*b* of driving elements 250 are engaged with complementary driving elements defined in the inner walls 54*a* of the driving opening 54. With the distal end 212*a* of the shaft 210 and the first end 222*a* of the sliding member 220 releasably locked in the driving opening 54 of the bone screw 51, a rotational force can be applied to the locking screwdriver 200 in order to cause the bone screw 51 to be driven into or backed out of the underlying structure.

When the bone screw 51 has been fully driven into or removed from the underlying structure, the locking screwdriver 200 can be operated from the releasably locked configuration to the retracted configuration. In accordance with the illustrated embodiment, a rotational force can be applied to the actuator 230 in a second rotation direction that is opposite the first rotation direction about the central axis CA, thereby causing the first and second pluralities of threads 237 and 219 to engage with one another, and causing the threaded knob 232 to advance proximally in the rearward direction along the shaft 210. As the threaded knob 232 advances proximally along the shaft 210, the first annular groove 239*a* will engage with the first tab 229*a*, thereby causing the sliding member 220 to translate in the rearward direction in the channel 214, away from the distal end 212*a* of the shaft 210. As the sliding member 220 translates proximally in the channel 214, the riding surfaces 223 will ride down along the corresponding sloped surfaces 213*a* of the plurality of ramps 213, causing the first end 222*a* of the sliding member 220 to be displaced radially inward within the driving opening 54 and the first and second pluralities 250*a* and 250*b* of driving elements 250 to disengage from the complementary driving elements defined in the inner walls 54*a* of the driving opening 54 and the interference lock to be released. The distal end 212*a* of the shaft 210 and the first end 222*a* of the sliding member 220 can then be removed from the driving opening 54 of the bone screw 51.

It should thus be appreciated that a method for releasably locking the locking screwdriver 200 to a bone anchor 50 can include the step of inserting the distal end 212*a* of the shaft 210 into a driving opening 54 of the bone anchor 50. The method can further include causing the sliding member 220 to translate along the shaft 210 in the forward direction and onto the ramps 213, for example by operating the actuator 230, thereby displacing the sliding member 220 along a direction substantially perpendicular to the forward direction so as to define an interference lock between the sliding member 220 and an inner surface 54*a* of the bone anchor 50, thereby releasably locking the sliding member 220 to the bone anchor 50. The method can further include causing the sliding member 220 to translate along a rearward direction that is substantially opposite the forward direction and at least partially off the ramps 213, for example by operating the actuator 230 in reverse, thereby unlocking the sliding member 220 from the bone anchor 50.

Although the components of the interlock driving instrument have been described herein with reference to one or both of preferred embodiments and preferred methods, it should be understood that the words which have been used herein are words of description and illustration rather than words of limitation, and that the interlock driving instrument is therefore not intended to be limited to the disclosed embodiments. Furthermore, the structure and features of each of the embodiments described above can be applied to the other embodiments described herein, unless otherwise indicated. Additionally, it should be appreciated that although the interlock driving instrument has been described herein with reference to one or more of particular structure, methods, and embodiments, the scope of the instant disclosure is not intended to be limited to those particulars, but rather is meant to extend to all structures, methods, and uses of the interlock driving instrument. Those skilled in the relevant art, having the benefit of the teachings of this specification, may effect numerous modifications to the interlock driving instrument as described herein, and changes may be made without departing from the scope and spirit of the instant disclosure, for instance as recited in the appended claims.

What is claimed:

1. A locking screwdriver configured to drive a bone anchor into bone, the locking screwdriver comprising:
    a shaft that defines a proximal end and a distal end that is spaced from the proximal end along a first direction, the distal end configured to be received by a driving opening of the bone anchor, the shaft defining a first guide member that extends from the distal end toward the proximal end along the first direction, the shaft including a plurality of ramps disposed at the distal end, each ramp defining a sloped surface that is angularly offset relative to the first direction, wherein the ramps are spaced apart from each other along a second direction that extends substantially perpendicular to the first direction;
    a sliding member that includes a second guide member configured to engage the first guide member so as to direct the sliding member to translate along the shaft and onto each of the plurality of ramps to a releasably locked position, wherein the locking screwdriver is releasably locked to the bone anchor when the sliding member and the distal end of the shaft are disposed in the driving opening and the sliding member is in the releasably locked position; and
    an actuator configured to apply a force that biases the sliding member to translate along the shaft to the releasably locked position.

2. The locking screwdriver of claim 1, wherein the first guide member comprises a channel that extends from the distal end toward the proximal end along the first direction, the channel defining a bottom surface along which the sliding member translates, at least one of the plurality of ramps extending outwardly from the bottom surface.

3. The locking screwdriver of claim 2, wherein the second guide member comprises a sliding surface configured to translate along the bottom surface of the channel, the sliding member includes a projection that extends outward from the sliding surface, and the shaft defines a groove that extends into the bottom surface from the distal end of the shaft toward the proximal end along the first direction, the projection configured to be received in the groove and to translate in the groove along the first direction.

4. The locking screwdriver of claim 3, wherein the projection extends from the sliding member along a centerline of the sliding member that extends substantially parallel relative to the first direction.

5. The locking screwdriver of claim 3, wherein the projection extends from the sliding surface along a third direction that extends substantially perpendicular to the first and second directions, respectively.

6. The locking screwdriver of claim 3, wherein the projection extends from the first end of the sliding member toward the second end along the first direction.

7. The locking screwdriver of claim 3, wherein the plurality of ramps comprises a pair of ramps, each ramp disposed adjacent a respective opposed side of the groove.

8. The locking screwdriver of claim 7, wherein the projection extends from the first end of the sliding member toward the second end along a centerline of the sliding member that extends substantially parallel relative to the first direction.

9. The locking screwdriver of claim 8, wherein the first end of the sliding member defines a pair of riding surfaces disposed along opposed sides of the projection, each riding surface configured to ride along a respective sloped surface of a respective one of the pair of ramps.

10. The locking screwdriver of claim 3, wherein the groove is configured such that the projection will not make contact with the groove when the sliding member is translated relative to the shaft.

11. The locking screwdriver of claim 2, wherein each of the plurality of ramps defines a respective transition location where the respective sloped surface of each ramp intersects with the channel, the transition location of each ramp spaced from the distal end of the shaft a distance that is shorter than a depth of the driving opening of the bone anchor.

12. The locking screwdriver of claim 11, wherein the respective transition locations of each of the plurality of ramps are equally spaced from the distal end of the shaft.

13. The locking screwdriver of claim 11, wherein the sloped surface of each ramp is straight between a respective top end of each ramp and the respective transition location of each ramp.

14. The locking screwdriver of claim 2, wherein the shaft includes at least one retaining member configured to retain the sliding member in the channel.

15. The locking screwdriver of claim 14, wherein the at least one retaining member comprises a pair of retaining members, each retaining member extending inwardly from a respective opposed side of the channel.

16. The locking screwdriver of claim 15, wherein each retaining member comprises an arced projection extending from a respective upper edge of a respective one of the opposed sides of the channel.

17. The locking screwdriver of claim 16, wherein the sliding member includes a retaining section configured to be disposed between the arced projections.

18. The locking screwdriver of claim 16, wherein the sliding member further comprises a pair of retention wings, each retention wing configured to be received by a corresponding one of the arced projections, such that engagement between the pair of retention wings and the pair of arced projections retains the sliding member in the channel.

19. The locking screwdriver of claim 1, wherein the sliding member includes at least one coupling member, the actuator defines at least one coupling interface configured to receive the at least one coupling member, and the actuator defines a threaded bore configured to engage complementary threads defined along at least a portion of an outer surface of the shaft.

20. The locking screwdriver of claim 19, wherein the at least one coupling member comprises a pair of tabs that extend outward from the sliding member proximate the second end of the sliding member, the tabs spaced apart from one another along the first direction, the actuator comprises a knob, and the at least one coupling interface comprises a pair of annular grooves that extend into opposed ends of the knob, each annular groove configured to receive a respective one of the pair of tabs.

21. A locking screwdriver comprising:
a shaft extending in a longitudinal direction between a proximal end and a distal end, a longitudinal channel extending into the shaft from the distal end, the channel defining a bottom surface that is sloped at the distal end of the shaft, the shaft defining retaining members along opposing sides of the channel, wherein each of the retaining members extends toward the other of the retaining members as it extends out from the bottom surface;
a sliding member disposed in the channel and captured within the channel by the retaining members with respect to movement of the sliding member away from the bottom surface, the sliding member translatable within the channel; and
an actuator operatively coupled to the shaft and to a second end of the sliding member, the actuator configured to translate the sliding member within the channel,
wherein the distal end of the shaft and a first end of the sliding member opposite the second end of the sliding member are configured to be concurrently received in a driving opening of a bone anchor such that when the first end of the sliding member rides along the sloped surface, the first end of the sliding member is displaced radially outward within the driving opening, releasably locking the distal end of the shaft and the first end of the sliding member within the driving opening of the bone anchor.

22. The locking screwdriver as recited in claim 21, wherein the actuator comprises a knob having a threaded bore extending therethrough and a coupling interface configured to receive complimentary coupling members defined on the sliding member, the threaded bore configured to rotatably engage complimentary threads defined on an outer surface of the shaft.

23. The locking screwdriver as recited in claim 22, wherein the coupling interface comprises a pair of annular grooves extending into the knob from opposing ends of the knob, the annular grooves configured to receive the coupling members.

24. The locking screwdriver as recited in claim 23, wherein the coupling members comprise a pair of tabs extending radially outward from the sliding member, each of the tabs configured to be received in a respective one of the annular grooves.

25. The locking screwdriver as recited in claim 21, wherein the retaining members of the shaft comprise a pair of arced protrusions extending inwardly from opposing upper edges of the channel.

26. The locking screwdriver as recited in claim 25, wherein the sliding member comprises a narrowed section, the narrowed section configured to be disposed between the arced protrusions.

27. The locking screwdriver as recited in claim 25, wherein the sliding member further comprises longitudinal wings configured to be received within the arced protrusions, engagement between the wings and the arced protrusions retaining the sliding member within the channel.

28. The locking screwdriver as recited in claim 21, wherein the sloped surface is flat between the distal end of the shaft and a transition into the bottom surface of the channel.

29. The locking screwdriver as recited in claim 21, wherein the sloped surface is curved between the distal end of the shaft and a transition into the bottom surface of the channel.

30. The locking screwdriver as recited in claim 21, wherein the first end of the sliding member defines a tip section with a sloped tip surface.

31. A locking screwdriver configured to drive a bone anchor into bone, the locking screwdriver comprising:
a shaft that defines a proximal end and a distal end that is spaced from the proximal end along a first direction, the distal end configured to be received by a driving opening of the bone anchor, the shaft defining a channel that defines a bottom surface and a groove that extends into the bottom surface from the distal end of the shaft toward the proximal end along the first direction, wherein the channel extends from the distal end toward the proximal end along the first direction, the shaft includes a plurality of ramps disposed at the distal end, each ramp defining a sloped surface that is angularly offset relative to the first direction, and at least one of the plurality of ramps extends outwardly from the bottom surface;
a sliding member that includes a sliding surface and a projection that extends outward from the sliding surface and is configured to be received in the groove and to translate in the groove along the first direction, such that the sliding surface translates along the bottom surface and directs the sliding member to translate along the shaft and onto each of the plurality of ramps to a releasably locked position, wherein the locking screwdriver is releasably locked to the bone anchor when the sliding member and the distal end of the shaft are disposed in the driving opening and the sliding member is in the releasably locked position; and an actuator configured to apply a force that biases the sliding member to translate along the shaft to the releasably locked position.

32. The locking screwdriver of claim 31, wherein the projection extends from the sliding member along a centerline of the sliding member that extends substantially parallel relative to the first direction.

33. The locking screwdriver of claim 31, wherein the projection extends from the sliding surface along a third direction that extends substantially perpendicular to the first and second directions, respectively.

34. The locking screwdriver of claim 31, wherein the projection extends from the first end of the sliding member toward the second end along the first direction.

35. The locking screwdriver of claim 31, wherein the plurality of ramps comprises a pair of ramps, each ramp disposed adjacent a respective opposed side of the groove.

36. The locking screwdriver of claim 35, wherein the projection extends from the first end of the sliding member toward the second end along a centerline of the sliding member that extends substantially parallel relative to the first direction.

37. The locking screwdriver of claim 36, wherein the first end of the sliding member defines a pair of riding surfaces disposed along opposed sides of the projection, each riding surface configured to ride along a respective sloped surface of a respective one of the pair of ramps.

38. The locking screwdriver of claim 31, wherein the groove is configured such that the projection will not make contact with the groove when the sliding member is translated relative to the shaft.

39. The locking screwdriver of claim 31, wherein the shaft includes at least one retaining member configured to retain the sliding member in the channel.

40. The locking screwdriver of claim 39, wherein the at least one retaining member comprises a pair of retaining members, each retaining member extending inwardly from a respective opposed side of the channel.

41. The locking screwdriver of claim 40, wherein each retaining member comprises an arced projection extending from a respective upper edge of a respective one of the opposed sides of the channel.

42. The locking screwdriver of claim 41, wherein the sliding member includes a retaining section configured to be disposed between the arced projections.

43. A locking screwdriver comprising:
a shaft extending in a longitudinal direction between a proximal end and a distal end, a longitudinal channel extending into the shaft from the distal end, the channel defining a bottom surface that is sloped at the distal end of the shaft, the shaft defining retaining members along opposing sides of the channel;
a sliding member disposed in the channel and retained within the channel by the retaining members, the sliding member translatable within the channel; and
an actuator operatively coupled to the shaft and to a second end of the sliding member, the actuator configured to translate the sliding member within the channel, wherein the actuator comprises a knob having a threaded bore extending therethrough, the threaded bore configured to rotatably engage complimentary threads defined on an outer surface of the shaft, the knob further having a coupling interface configured to receive complimentary coupling members defined on the sliding member, the coupling interface comprising a pair of annular grooves that extend into the knob from opposing ends of the knob, the annular grooves configured to receive the coupling members,
wherein the distal end of the shaft and a first end of the sliding member opposite the second end of the sliding member are configured to be concurrently received in a driving opening of a bone anchor such that when the first end of the sliding member rides along the sloped surface, the first end of the sliding member is displaced radially outward within the driving opening, releasably locking the distal end of the shaft and the first end of the sliding member within the driving opening of the bone anchor.

44. The locking screwdriver as recited in claim 43, wherein the coupling members comprise a pair of tabs extending radially outward from the sliding member, each of the tabs configured to be received in a respective one of the annular grooves.

45. The locking screwdriver as recited in claim 43, wherein the retaining members of the shaft comprise a pair of arced protrusions extending inwardly from opposing upper edges of the channel.

46. The locking screwdriver as recited in claim 45, wherein the sliding member comprises a narrowed section, the narrowed section configured to be disposed between the arced protrusions.

47. The locking screwdriver as recited in claim 45, wherein the sliding member further comprises longitudinal wings configured to be received within the arced protrusions, engagement between the wings and the arced protrusions retaining the sliding member within the channel.

* * * * *